(12) United States Patent
Dennis et al.

(10) Patent No.: US 7,396,529 B2
(45) Date of Patent: Jul. 8, 2008

(54) COMPOSITIONS AND METHODS FOR REGULATING RECEPTOR CLUSTERING

(75) Inventors: Jim Dennis, Etobicoke (CA); Michael Demetriou, Irvine, CA (US)

(73) Assignee: Mount Sinai Hospital, Toronto (CA)

( * ) Notice: Subject to any disclaimer, the term of this patent is extended or adjusted under 35 U.S.C. 154(b) by 434 days.

(21) Appl. No.: 10/250,935

(22) PCT Filed: Jan. 11, 2002

(86) PCT No.: PCT/CA02/00002

§ 371 (c)(1),
(2), (4) Date: Dec. 15, 2003

(87) PCT Pub. No.: WO02/055728

PCT Pub. Date: Jul. 18, 2002

(65) Prior Publication Data

US 2004/0082009 A1 Apr. 29, 2004

Related U.S. Application Data

(60) Provisional application No. 60/261,516, filed on Jan. 12, 2001.

(51) Int. Cl.
*C07K 17/00* (2006.01)
*C12N 5/00* (2006.01)
(52) U.S. Cl. ..................... 424/133.1; 435/7.2; 435/375; 530/395
(58) Field of Classification Search ........................ None
See application file for complete search history.

(56) References Cited

FOREIGN PATENT DOCUMENTS

WO      WO 99/12041      3/1999

OTHER PUBLICATIONS

Demetriou et al., Nature Feb. 8, 2001 409(6821):733-9.*
Rabinovitch et al., Immunology 1999 97:100-106.*
Granovsky et al., Nature Medicine, Mar. 2000, 6(3):306-312.*
Dennis et al., Biochemica et Biophysica Acta. 1999;1473:21-31.*
Ki-Young Do, et al., J Biol Chem. Sep. 23, 1994;269(38):23456-23464.*
Palcic et al., J Biol Chem. Apr. 25, 1990;265(12):6759-6769.*
Cummings et al., J Biol Chem. Nov. 25, 1982; 257(22):13421-13427.*
Lemaire et al., J Biol Chem. Mar. 18, 1994;269(11):8069-8074.*
Essentials of Glycobiology. Varki et al., Eds. Cold Spring Harbor Laboratory Press. 1999. New York. pp. 2-3, and 538-540.*
Andersen et al., Curr Opin Biotech 1994 5:546-549.*

(Continued)

*Primary Examiner*—Manjunath Rao
*Assistant Examiner*—Cherie Woodward
(74) *Attorney, Agent, or Firm*—Merchant & Gould P.C.

(57) ABSTRACT

The invention relates to isolated complexes comprising one or more galectin associated with Mgat5 modified glycan or polylactosamine modified glycan, and isolated lectin-Mgt5 modified glycan lattice comprising an array of multivalent interactions among lectins, Mgat5 modified glycans, polylactosamine modified glycans, and/or glycoproteins. Methods for evaluating a test compound for its ability to regulate receptor clustering through glycans on cell surfaces; and methods for regulating receptor clustering on cell surfaces comprising altering glycans on the cell surface associated with receptor clustering are also discovered.

4 Claims, 4 Drawing Sheets

OTHER PUBLICATIONS

Goochee et al., Biotechnology, Dec. 9, 1991:1347-1355.*
Barkai et al., 1997, Nature 387: 913-917, "Robustness in simple biochemical networks".
Barondes et al., 1994, Cell 76: 597-598, "Galectins: A Family of Animal β-Galactoside-Binding Lectins".
Chung et al., 2000, The Journal of Immunology 165: 3722-3729, "Galectin-1 Induces Partial TCR ζ-Chain Phosphorylation and Antagonizes Processive TCR Signal Transduction".
Cummings et al., 1984, The Journal of Biological Chemistry 259: 6253-6260, "The Distribution of Repeating [Galβ1,4GlcNAcβ1,3] Sequences in Asparagine-linked Oligosaccharides of the Mouse Lymphoma Cell Lines BW5147 and PHA$^R$ 2.1".
Cummings et al., 1982, The Journal of Biological Chemistry 257: 13421-13427, "A Mouse Lymphome Cell Line Resistant to the Leukoagglutinating Lectin from Phaseolus vulgaris Is Deficient In UDP-GlcNAc: α-D-mannoside β1,6 N-Acetylglucosaminyltransferase".
Downward et al., 1990, Nature 346: 719-723, "Stimulation of p21$^{ras}$ upon T-cell activation".
Ellies et al., 1998, Immunity 9: 881-890, "Core 2 Oligosaccharide Biosynthesis Distinguishes between Selectin Ligands Essential for Leukocyte Homing and Inflammation".
Granovsky et al., 2000, Nature Medicine 6: 306-312, "Suppression of tumor growth and metastasis in Mgat5-deficient mice".
Gu et al., 1993, J. Biochem 113: 614-619, "Purification and Characterization of UDP-N-Acetylglucosamine: α-6-D-Mannoside β1-6N-Acetylglucosaminyltranferase (N-Acetylglucosaminyltransferase V) from a Human Lung Cancer Cell Line".
Hadari et al., 1995, The Journal of Biological Chemistry 270: 3447-3453, "Galectin-8".
Hubbard et al., 1986, Proc. Natl. Acad. Sci. 83: 1852-1856, "Glycosylation of the T-Cell Antigen-Specific Receptor And Its Potential Role In Lectin-Mediated Cytotoxicity".
Karsan et al., 1998, J. Clin. Invest. 101: 2438-2445, "Leukocyte Adhesion Deficiency Type II Is A Generalized Defect of De Novo GDP-Fucose Biosynthesis".
Knibbs et al., 1993, The Journal of Biological Chemistry 1993: 14940-14947, "Carbohydrate-binding Protein 35".
Lafaille et al., 1994, Cell 78: 399-408, "High Incidence of Spontaneous Autoimmune Encephalomyelitis in Immunodeficient Anti-Myelin Basic Protein T Cell Receptor Transgenic Mice".
Moloney et al., 2000, Nature 406: 369-375, "Fringe is a glycosyltransferase that modifies Notch".
Monks et al., 1998, Nature 395: 82-86, "Three-dimensional segregation of supramolecular activation clusters in T cells".
Offner et al., 1990, Journal of Neuroimmunology 28: 177-184, "Recombinant human β-galactoside binding lectin suppresses clinical and histological signs of experimental autoimmune encephalomyelitis".
Oliveira-dos-Santos et al., 1999, The Journal of Immunology 162: 4490-4495, "CD28 Costimulation Is Crucial for the Development of Spontaneous Autoimmune Encephalomyelitis".
Pace et al., 1999, The Journal of Immunology 163: 3801-3811, "Restricted Receptor Segregation into Membrane Microdomains Occurs on Human T Cells During Apoptosis Induced by Galectin-1".
Palcic et al., 1990, The Journal of Biological Chemistry 265: 6759-6769, "Regulation of N-Acetylglucosaminyltransferase V Activity".
Paulson et al., 1989, The Journal of Biological Chemistry 264: 17615-17618, "Glycosyltransferases".
Perillo et al., 1995, Nature 378: 736-739, "Apoptosis of T Cells Mediated by Galectin-1".
Priatel et al., 2000, Immunity 12: 273-283, "The ST3Gal-l Sialytransferase Controls CD8$^+$ T Lymphocyte Homeostasis by Modulating O-Glycan Biosynthesis".

Reich et al., 1997, Nature 387: 617-620, "Ligand-specific oligomerization of T-cell receptor molecules".
Reif et al., 1998, Immunity 8: 395-401, "Networking Rho Family GTPases in Lymphocytes".
Rudd et al., 1999, J. Mol. Biol. 293: 351-366, "Roles for Glycosylation of Cell Surface Receptors Involved in Cellular Immune Recognition".
Saito et al., 1994, Biochemical and Biophysical Research Communications 198: 318-327, "cDNA cloning and chromosomal mapping of human N-acetylglucosaminyltransferase V$^*$".
Sato et al., 1992, The Journal of Biological Chemistry 267: 6983-6990, "Binding Specificity of a Baby Hamster Kidney Lectin for H Type I and II Chains, Polylactosamine Glycans, and Appropriately Glycosylated Forms of Laminin and Fibronectin".
Schachter et al., Biochem. Cell Biol. 64: 163-181, "Biosynthetic controls that determine the branching and microheterogeneity of protein-bound oligosaccharides".
Shoreibah et al., 1993, The Journal of Biological Chemistry 268: 15381-15385, "Isolation, Characterization, and Expression of a cDNA Encoding N-Acetylglucosaminyltransferase V".
Trevillyan et al., 1990, The Journal of Immunology 145: 3223-3230, "Differential Inhibition of T Cell Receptor Signal Transduction and Early Activation Events by a Selective Inhibitor of Protein-Tyrosine Kinase".
Valltutti et al., 1995, Nature 375: 148-151, "Serial triggering of many T-cell receptors by a few peptide-MHC complexes".
Vespa et al., 1999, The Journal of Immunology 162: 799-806, "Galectin-1 Specifically Modulates TCR Signals to Enhance TCR Apoptosis but Inhibit IL-2 Production and Proliferation".
Viola et al., 1999, Science 283: 680, "T Lymphocyte Costimulation Mediated by Reorganization of Membrane Microdomains".
Viola et al., 1996, Science 273: 104-106, "T Cell Activation Determined by T Cell Receptor Number and Tunable Thresdholds".
Wall et al., 1988, Proc. Natl. Acad. Sci. USA 85: 5644-5648, "Inhibitors of glycoprotein processing alter T-cell proliferative responses to antigen and to interleukin 2".
Wang et al., 1998, The EMBO Journal 17: 10-26, "Atomic structure of an αβ T cell receptor (TCR) heterodimer in complex with an anti-TCR Fab fragment derived form a mitogenic antibody".
Wulfing et al., 1998, Science 282: 2266, "A Receptor/Cytoskeletal Movement Triggered by Costimulation During T Cell Activation".
Demetriou Michael et al.: "Negative regulation of T-cell activation and autoimmunity by Mgat5 N-glycosylation." Nature (London) vol. 409, No. 6821, 2001, pp. 733-739.
Granovsky Maria et al: "Mgat5 N-glycans regulate integrin and T cell receptor functions affecting cancer development and immune responses in vivo." Glycoconjugate Journal, vol. 17, No. 1-2, Jan. 2000 p. 26 XP009005350 Second International Glycosyltransferase Symposium; Toronto, Ontario, Canada; May 12-14, 2000 ISSN: 0282-0080.
Dennis James W et al: "Glycoprotein glycosylation and cancer progression." Biochimica et Biophysica Acta, vol. 1473, No. 1, Dec. 6, 1999, pp. 21-34, XP001145594 ISSN: 0006-3002.
Rabinovich G A et al: "Specific inhibition of T-cell adhesion to extracellular matrix and proinflammatory cytokine secretion by human recombinant galectin-1." Immunology, ₁ vol. 97, No. 1, May 1999, pp. 100-106, XP001121122 ISSN: 0019-2805.
Cummings et al: "P-selectin and galectin interactions with human neutrophils" Proceedings of the ACS International Symposium on Recent Advances in Polyolefins, XX, XX, No. Part 1, Mar. 29, 1998, p. XP002090743.
Perillo N L et al: "Apoptosis of T Cells Mediated by Galectin-1". Nature, Macmillan Journals Ltd. London, GB, vol. 378, No. 6558, Dec. 14, 1995, pp. 736-739, XP002034768 ISSN: 0028-0836.

* cited by examiner

COMPOSITIONS AND METHODS FOR REGULATING RECEPTOR CLUSTERING

FIELD OF THE INVENTION

The invention relates to complexes, lattices, compositions and methods for regulating receptor clustering on cell surfaces.

BACKGROUND OF THE INVENTION

N- and O-linked glycans are found on both cell-surface and secreted proteins, many of which control proliferation and cell fate decisions in animals. Tissue-specific expression of glycosyltransferases is a significant factor controlling the glycan profiles observed in differentiated cells (Paulson, Jc and Colley K J, J Biol Chem 1989, 264:17615-17618). In addition, many glycosyltransferases compete for acceptor intermediates causing bifurcations of the pathways and additional structural complexity (Schachter H, Biochem Cell Biol 1986, 64:163-181).

Specific glycan structures regulate lymphocyte adhesion, re-circulation and maturation as demonstrated by the GDP-fucose deficiency in LADII patients (11), and immune defects associated with C2 GlcNAc-T(L) (12) or ST3Gal-I (13) mutant mice. Depletion of the β1,6N-acetylglucosaminyl-transferase V (Mgat5) modified glycans by swainsonine, an inhibitor of α-mannosidase II, potentiates antigen-dependent T cell proliferation, however, the molecular basis of this effect is unknown (14). Mgat5 catalyzes the addition of β1,6GlcNAc to N-glycan intermediates found on newly synthesized glycoproteins transiting the medial Golgi (15) (FIG. 1A). The glycans are elongated in trans-Golgi to produce tri (2,2,6) and tetra (2,4,2,6) antennary N-glycans which are preferentially extended with N-acetyllactosamine (Galβ1GlcNAc) and polymeric forms of N-acetyllactosamine also known as polylactosamine (6).

SUMMARY OF THE INVENTION

Applicants have demonstrated that differential receptor glycosylation effects ligand-dependent clustering of receptors. Applicants illustrated the effects of differential receptor glycosylation with T cell receptors (TCR). T cell activation requires clustering of a threshold number of T cell receptors (TCR) at the site of antigen presentation, a number that is reduced by CD28 co-receptor recruitment of signaling proteins to TCR (1-5). Applicants demonstrate that a deficiency in β1,6N-acetylglucosaminyltransferase V (Mgat5), an enzyme in the N-glycosylation pathway, lowers T cell activation thresholds by directly enhancing TCR clustering. Mgat5-deficient mice displayed kidney autoimmune disease, enhanced delayed type hypersensitivity, and increased susceptibility to experimental autoimmune encephalomyelitis. Thus, dysregulation of Mgat5 in humans may increase susceptibility to autoimmune diseases such as multiple sclerosis.

Recruitment of TCR to agonist-coated beads, TCR signaling, actin microfilament reorganization and agonist-induced proliferation were enhanced in Mgat5$^{-/-}$ T cells. Mgat5 initiates GlcNAc β1,6 branching on N-glycans, thereby increasing N-acetyllactosamine (6), the lectin for galectins (7, 8) proteins known to modulate T cell proliferation and apoptosis (9, 10). Indeed, galectin-3 was associated with the TCR complex at the cell surface, an interaction dependent on Mgat5. Pre-treatment of wild type T cells with lactose to compete for galectin binding produced a phenocopy of Mgat5$^{-/-}$ TCR clustering. These data indicate that a galectin-glycoprotein lattice strengthened by Mgat5-modified glycans restricts TCR recruitment to the site of antigen presentation.

In accordance with an aspect of the invention an isolated complex is provided comprising one or more lectin (e.g. a galectin) associated or interacting with a Mgat5 modified glycan or polylactosamine modified glycan that is associated with receptor clustering. The invention also provides a peptide derived from the binding domain of a lectin, preferably a galectin, that interacts with a Mgat5 modified glycan, or a polylactosamine modified glycan; and, an oligosaccharide derived from a Mgat5 modified glycan or a polylactosamine modified glycan that interacts with one or more lectin (e.g. a galectin). The invention also contemplates antibodies specific for these complexes, peptides, and oligosaccharides.

The invention also contemplates an isolated lectin-Mgat5 modified glycan lattice comprising an array of multivalent interactions among lectins, Mgat5 modified glycans, polylactosamine modified glycans, and/or glycoproteins that are associated with receptor clustering. The Mgt5 modified glycans and polylactosamine modified glycans are preferably part of glycoproteins of receptors including but not limited to TCR, growth factor receptors, and cytokine receptors.

Still farther the invention provides a method for evaluating a test compound for its ability to regulate receptor clustering through glycans on cell surfaces (e.g. through Mgat 5 modified glycans and/or polylactosamine modified glycans) comprising assaying for alterations of the glycans in the presence of the test compound. Alterations of the glycans may increase or enhance, or inhibit or decrease receptor clustering thereby modifying signal transduction by the receptors.

In an aspect of the invention, a method is provided for evaluating a test compound for its ability to regulate receptor clustering through a lectin-Mgat5 modified glycan lattice, in particular a galectin-Mgat5 modified glycan lattice comprising determining the effect of the test compound on the lattice or a component thereof. A test compound may be a substance that interacts with a component of a lectin-Mgat5 modified glycan lattice. In particular, the substance may interact with a lectin (e.g. galectin), Mgat5 modified glycan, or polylactosamine modified glycan. The substance may be a molecule derived from a lectin (e.g. galectin), Mgat3 modified glycan, polylactosamine modified glycan, or lectin-Mgat5 modified glycan lattice; or, a substance which inhibits or enhances the interaction of a lectin (e.g. galectin) and a component of a lectin –Mgat5 modified glycan lattice (e.g. the interaction of a galectin and Mgat5 modified glycan and/or polylactosamine modified glycan).

In an embodiment, the method comprises (a) mixing a galectin-Mgat5 modified glycan lattice, or a galectin and one or more of a Mgat5 modified glycan and a polylactosamine modified glycan, and a test compound, under conditions which maintain the lattice or permit the formation of complexes between the galectin and one or more glycan; and (b) removing and/or detecting galectin-Mgat5 modified glycan lattice, complexes, galectin, Mgat5 modified glycan, or polylactosamine modified glycan.

The invention also encompasses the compounds identified using methods of the invention.

The invention also contemplates cell-based assays. In an aspect of the invention, a method is provided comprising (a) providing cells with receptors whereby clustering of the receptors is regulated through a lectin-Mgat5 modified glycan lattice or a component thereof; (b) mixing the cells, lectin, and a test compound under conditions which permit the formation of a lectin-Mgat5 modified glycan lattice, complexes between a lectin and one or more glycan of the lattice, and/or receptor clustering; (c) detecting a lectin-Mgat5 modified glycan lattice, complexes, lectin, Mgat5 modified glycan, polylactosamine modified glycan, alterations to the lattice, complexes, lectin, Mgat5 modified glycan, or polylactosamine modified glycan, or receptor clustering; and (d) comparing to a control to determine if the test compound alters the lectin-Mgat5 modified glycan lattice or component thereof and potentially regulates receptor clustering.

Differential glycosylation of receptors has been found to alter receptor clustering. Receptor clustering or oligomerization is a requisite event for signal transduction of receptors, including but not limited to receptors that stimulate immune reactions, growth factor receptors, and cytokine receptors. Thus, differences in glycans (e.g. Mgat5 modified glycans or polylactosame modified glycans) on cell surfaces that are associated with clustering of receptors including receptors that stimulate immune reactions (e.g. T cell receptors, Ig receptors, B cell receptors, NK receptors), the HER family of transmembrane receptor tyrosine kinases [e.g. epidermal growth factor (EGF) receptor also known as HER1 or Erb1, HER2 (neu, Erb2), HER3 (Erb3), and HER4 (Erb4)], cadherin receptors (e.g. E-cadherin and N-cadherin), interleukin (IL) receptors including IL-2 receptor, TNFγ receptor, and integrins, may affect clustering or oligomerization of these receptors.

The invention provides a method for regulating receptor clustering on cell surfaces comprising altering glycans on the cell surface associated with receptor clustering. In an aspect the invention provides a method for activating signal transduction in a cell with receptors that cluster or oligomerize to thereby initiate signal transduction comprising altering glycans associated with clustering or oligomerization of the receptors.

Glycans can be altered by modulating one or more glycosyltransferase enzyme involved in the synthesis of the glycans, in particular N-glycans and N-glycan intermediates. Altering glycans may involve increasing or decreasing Mgat5 modified glycans or polylactosamine modified glycans associated with clustering of the receptors. In a preferred embodiment, an enzyme involved in the synthesis of the glycans is modulated (e.g. Mgat5).

In accordance with the present invention, a method is provided for regulating receptor clustering on cell surfaces, in particular ligand-dependent receptor clustering, more particularly T cell receptor clustering, comprising modulating Mgat5 activity, the amount of Mgat5 modified glycans, polylactosamine modified glycans, or lectin-Mgat5 modified glycan lattice, or the amount of binding or interaction of one or more components of a lectin-Mgat5 modified glycan lattice, (e.g. Mgat5 modified glycans or polylactosamine modified glycans with lectins that bind to the glycans, for example, galectins).

In accordance with another aspect of the invention, a method is provided for treating or preventing a condition associated with decreased or increased receptor clustering or a receptor clustering defect in a subject comprising altering glycans associated with receptor clustering. Glycans can be altered by modulating a glycosyltransferase enzyme (e.g. Mgat5) involved in the synthesis of the glycans.

In accordance with a particular aspect of the invention, a method is provided for treating or preventing a condition associated with decreased or increased receptor clustering (more particularly T cell receptor clustering), or a receptor clustering defect (more particularly a T cell receptor clustering defect), comprising modulating Mgat5 activity, the amount of Mgat5 modified glycans, polylactosamine modified glycans, or lectin-Mgat5 modified glycan lattice, and/or the amount of binding or interaction of one or more components of a lectin-MgatV modified glycan lattice (e.g. a galectin, a Mgat5 modified glycan, polylactosamine modified glycan, or glycoproteins).

The invention also contemplates compounds for regulating receptor clustering. The compounds may be capable of directly or indirectly modifying glycans involved in receptor clustering. Such compounds may modulate the activity of an enzyme involved in the synthesis of the glycans (e.g. a glycosyltransferase such as Mgat5), the amount of the glycans, (e.g. the amount of Mgat5 modified glycans or polylactosamine glycans), and/or the amount of binding of the glycans with a substance that binds to the glycans thereby regulating receptor clustering (e.g. the binding or interaction of Mgat5 modified glycans and galectins). The invention also provides methods for assaying for such compounds. Compositions comprising such compounds are also within the scope of the invention.

In accordance with an aspect of the invention there is provided a method of, and products for, diagnosing and monitoring conditions characterized by an abnormality in clustering of a receptor comprising assaying for differential glycosylation of the receptor. Differential glycosylation may be assayed by determining the presence of Mgat5 modified glycans, polylactosamine modified glycans, lectin-Mgat5 modified glycan lattice, or an alteration or change in such glycans or lattice, compared to a control.

The invention relates to the control of glycan-lectin combinations (e.g. glacetin-polylactosamine modified glycan lattice) identified using the invention.

These and other aspects, features, and advantages of the present invention should be apparent to those skilled in the art from the following drawings and detailed description.

DESCRIPTION OF THE DRAWINGS

The invention will now be described in relation to the drawings in which.

DETAILED DESCRIPTION OF THE INVENTION

Figure 1:
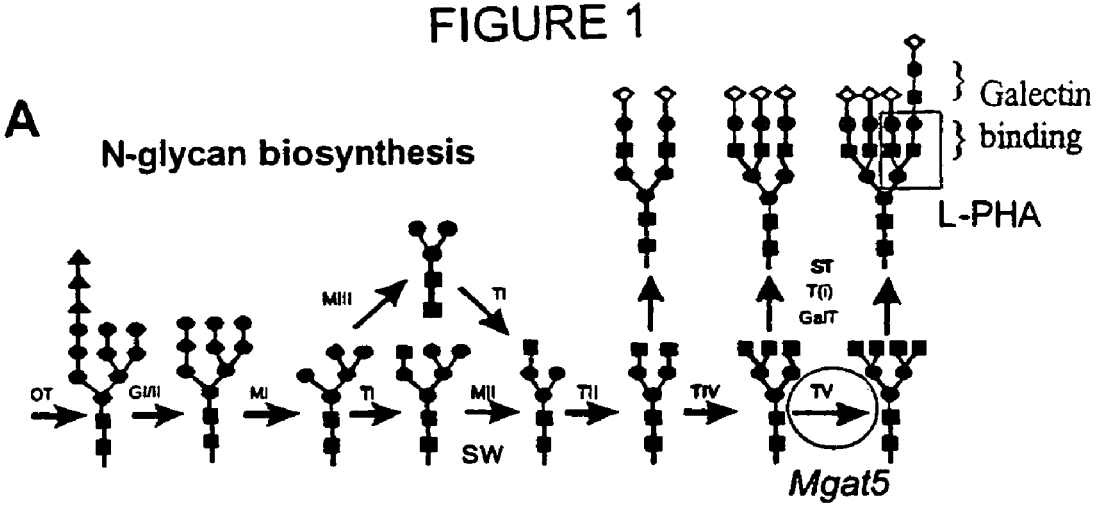
FIG. 1 Immune phenotype in Mgat5$^{-/-}$ mice (A) Schematic of the Golgi N-glycan biosynthesis pathway shows Mgat5 (TV) in the production of a tetra (2,4,2,6) antennary (numbers in brackets refer to the linkages of the antennae left to right). Abbreviations are oligosaccharyltransferase, OT; the α-glucosidases, GI, GII; the β-N-acetylglycosaminyltransferases, TI, TII, TIV, TV T(i); the α1,2mannosidases, MI, α1,3/6mannosidases MII, MIII: β1,4-galactosyltransferases, Gal-T; α-sialyltransferases, ST; SW, position of swainsonine block. The boxed structure Galβ1,4GlcNAcβ1, 6(Galβ1,4GlcNAcβ1,2)Manα binds L-PHA. The galectin binding disaccharide N-acetyllactosamine (Galβ1,4GlcNAc) is present in all antennae, and units are marked with red brackets in polylactosamine. (B) Distribution of CD4+ and CD8+ cells in spleen and thymus by FACS analysis using FITC- or phycoerythrin (PE)-conjugated antibodies (Pharmingen) reactive to CD3ε, CD4, and CD8. (C) TCR complex staining of spleen cells by FITC-anti-CD3ε antibodies and FACS analysis. (D) Light microscopy of kidney showing cresentic glomerulonephritis with a large crescent (CR) of mononuclear cells and fibrin obliterating the Bowman's space (BS) in Mgat5$^{-/-}$ mice. (E) DTH inflammatory response in Mgat5$^{-/-}$ (●) and Mgat5$^{+/+}$ (□) mice exposed to oxazolone first on their back, then 4 days later on the right ear. The results are plotted as mean change ±S.E. in ear thickness relative to the vehicle-treated left ear for 7 Mgat5$^{-/-}$ and 6 Mgat5$^{+/+}$ control littermates. P<0.01 with a student t test comparing the genotypes at 2-5 days.
Figure 1:
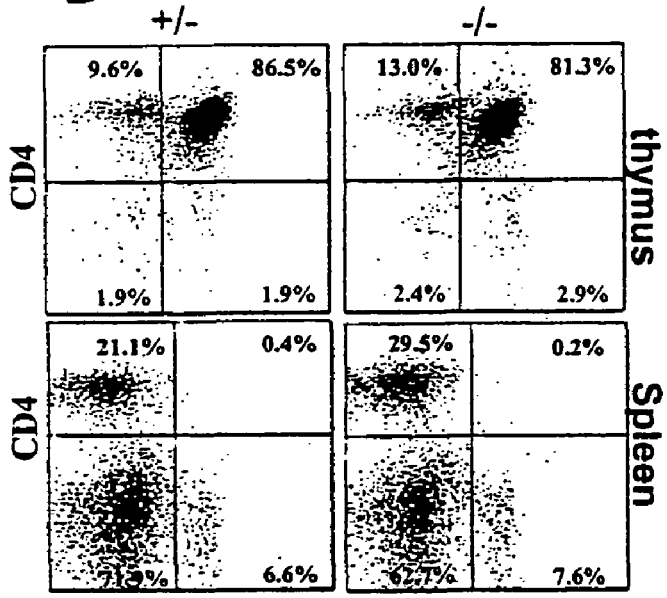
Figure 1:
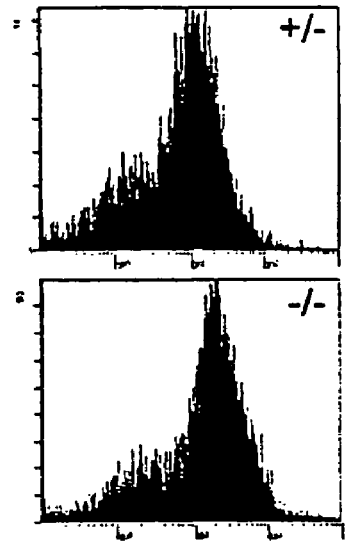
Figure 1:
Figure 1:
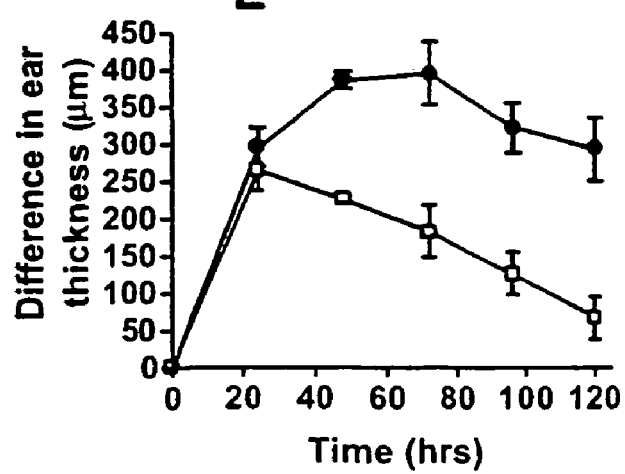

In accordance with the present invention there may be employed conventional biochemistry, enzymology, molecular biology, microbiology, and recombinant DNA techniques within the skill of the art. Such techniques are explained fully in the literature. See for example, Sambrook, Fritsch, & Maniatis, Molecular Cloning: A Laboratory Manual, Second Edition (1989) Cold Spring Harbor Laboratory Press, Cold Spring Harbor, N.Y.); DNA Cloning: A Practical Approach, Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B. D. Hames & S. J. Higgins eds (1984); Animal Cell Culture R. Freshney, ed. (1986); Immobilized Cells and enzymes IRL Press, (1986); and B. Perbal, A Practical Guide to Molecular Cloning (1984).

Complexes, Peptides, and Oligosaccharides

In accordance with an aspect of the invention an isolated complex is provided comprising one or more lectin associated or interacting with a Mgat5 modified glycan, or polylactosamine modified glycan that is associated with receptor clustering.

The term "isolated complex" refers to a complex substantially free of cellular material or culture medium when produced in vitro, or chemical reactants, or other chemicals when chemically synthesized.

"Lectin" refers to a molecule that interacts with, binds, or crosslinks carbohydrates. Preferably a lectin employed in the present invention interacts with, binds, or crosslinks Mgat5 modified glycans polylactosamine modified glycans, and/or glycoproteins. In an embodiment, the lectin is a galactose-binding protein, preferably a galectin.

"Galectin" refers to a member of the galectin family of beta-galactoside-binding proteins (see "Galectins: A Family of Animal beta-Galactoside-Binding Lectins" (1994) by S. H. Barondes, V. Castronovo, D. N. W. Cooper, R. D. Cummings, K. Drickamer, et al., In Cell 76, 597-598). Galectins includes lectins that bind beta-galactoside carbohydrate moieties in a thiol-dependent manner. (Reviewed in Hadari, Y. R. et al. (1998) J. Biol. Chem. 270:3447-3453.) Galectins are widely expressed and developmentally regulated. Galectins contain a characteristic carbohydrate recognition domain (CRD). The CRD is about 140 amino acids and contains several stretches of about 1-10 amino acids that are highly conserved among all galectins. Examples of galectins are galectin-1 through -10. In preferred embodiments of the invention, the galectin is galectin-3. Galectin-3 has one CRD, a short N-terminal domain and an intervening proline, glycine and tyrosine-rich domain which consists of repeats of 7-10 conserved amino acids. A "galectin" may be a monomer, dimer, or tetramer, preferably a dimer.

"Glycosyltransferase" refers to an enzyme involved in the synthesis of glycans, preferably the synthesis of N-glycans or O-glycans, more preferably N-glycans, most preferably tri (2,2,6) and tetra (2,4,2,6) antennary N-glycans, which are preferentially extended with N-acetyllactosamine and polylactosamine (i.e. polylactosamine modified glycan). Examples of such glycosyltransferase enzymes are Mgat5, core 2 GlcNAc transferase, GlcNAcT(i), and β1,4 galactosyltransferase. The term "glycosyltransferase" includes a wild type enzyme, or part thereof, or a mutant, variant or homolog of such an enzyme.

"Mgat5" refers to β1,6N-acetylglucosaminyltransferase V enzymes, preferably mammalian enzymes, that catalyze the addition of N-acetylglucosamine in beta 1-6 linkage to the alpha-linked mannose of biantennary N-linked oligosaccharides. Examples of Mgat5 enzymes are found on the ExPASy proteomics server as Enzyme: 2.4.1.155, and include human Mgat5 (Saito et al, 1994; gb:d17716, sw:q09328), and rat Mgat5 (Shoreibah et al 1993, J. Biol. Chem. 268: 15381-15385; gb114284, sw:q08834). "Mgat5" includes the wild type enzyme, or part thereof, or a mutant, variant or homolog of such an enzyme.

The term "wild type" refers to a polypeptide having a primary amino acid sequence which is identical with the native enzyme (for example, the human or mouse enzyme). The term "mutant" refers to a polypeptide having a primary amino acid sequence which differs from the wild type sequence by one or more amino acid additions, substitutions or deletions. Preferably, the mutant has at least 90% sequence identity with the wild type sequence. Preferably, the mutant has 20 mutations or less over the whole wild-type sequence. More preferably the mutant has 10 mutations or less, most preferably 5 mutations or less over the whole wild-type sequence.

The term "variant" refers to a naturally occurring polypeptide that differs from a wild-type sequence. A variant may be found within the same species (i.e. if there is more than one isoform of the enzyme) or may be found within a different species. Preferably the variant has at least 90% sequence identity with the wild type sequence. Preferably, the variant has 20 mutations or less over the whole wild-type sequence. More preferably, the variant has 10 mutations or less, most preferably 5 mutations or less over the whole wild-type sequence.

The term "part" indicates that the polypeptide comprises a fraction of the wild-type amino acid sequence. It may comprise one or more large contiguous sections of sequence or a plurality of small sections. The polypeptide may also comprise other elements of sequence, for example, it may be a fusion protein with another protein (such as one which aids isolation or crystallization of the polypeptide). Preferably the polypeptide comprises at least 50%, more preferably at least 65%, most preferably at least 80% of the wild-type sequence.

The term "homolog" means a polypeptide having a degree of homology with the wild-type amino acid sequence. The term "homology" refers to a degree of complementarity. There may be partial homology or complete homology. In an embodiment of the invention a glycostyltransferase, in particular Mgat5, is substantially homologous to a wild type enzyme. A sequence that is "substantially homologous" refers to a partially complementary sequence that at least partially inhibits an identical sequence from hybridizing to a target nucleic acid. Inhibition of hybridization of a completely complementary sequence to the target sequence may be examined using a hybridization assay (e.g. Southern or northern blot, solution hybridization, etc.) under conditions of reduced stringency. A sequence that is substantially homologous or a hybridization probe will compete for and inhibit the binding of a completely homologous sequence to the target sequence under conditions of reduced stringency. However, conditions of reduced stringency can be such that non-specific binding is permitted, as reduced stringency conditions require that the binding of two sequences to one another be a specific (i.e., a selective) interaction. The absence of non-specific binding may be tested using a second target sequence which lacks even a partial degree of complementarity (e.g., less than about 30% homology or identity). The substantially homologous sequence or probe will not hybridize to the second non-complementary target sequence in the absence of non-specific binding.

A sequence of an enzyme contemplated by the invention may have at least 60%, 65%, 70%, 75%, 80%, 85%, 90%, 95%, or 99% identity. The phrases "percent identity" or "% identity" refer to the percentage comparison of two or more amino acid or nucleic acid sequences. Percent identity can be determined electronically using for example the MegAlign program (DNASTAR, Inc., Madison Wis.). The MegAlign program can create alignments between two or more sequences according to different methods, e.g., the Clustal method. (See, e.g., Higgins, D. G. and P. M. Sharp (1988) Gene 73:237-244.) Percent identity between nucleic acid sequences can also be determined by other methods known in the art e.g., the Jotun Hein method. (See, e.g., Hein, J. (1990) Methods Enzymol. 183:626-645.) In addition, identity between sequences can be determined by other methods known in the art, e.g., by varying hybridization conditions.

"Mgat5 modified glycan" refers to a GlcNAcβ1,6Manα1, 6-branched N-glycan structure. The glycans are produced by Mgat5 which catalyzes the addition of Pl,6GlcNAc to N-glycan intermediates found on newly synthesized glycoproteins transiting the medial Golgi (15). The glycans are elongated in trans-Golgi to produce tri (2,2,6) and tetra (2,4,2,6) antennary N-glycans. A Mgat5 modified glycan may be substituted with for example polylactosamine (i.e. it may be a polylactosamine modified glycan). A Mgat5 modified glycan may be part of or covalently linked to a cell surface glycoprotein, including a glycoprotein of the T cell receptor complex.

"Polylactosamine modified glycan" refers to specific glycan structures comprising N-acetyllactosamine (Galβ1, 4GlcNAc) and polymeric forms of N-acetyllactosamine, also known as poly N-acetyllactosamine or polylactosamine (6). Preferably the polylactosamine modified glycan is an Mgat5 modified glycan substituted with poly N-acetyllactosamine. A polylactosamine modified glycan may be part of or covalently linked to a cell surface glycoprotein, including a glycoprotein of the T cell receptor complex.

The invention also contemplates a lectin-Mgat5 modified glycan lattice, preferably a galectin-Mgat5 modified glycan lattice.

A "lattice" is an arrangement of multiple interacting molecules, in particular, an arrangement or array of mulitvalent interactions among lectins, glycans, and/or glycoproteins. A preferred lattice of the invention is a lectin-Mgat5 modified glycan lattice.

A "lectin-Mgat5 modified glycan lattice" refers to a lattice formed from the multivalent interactions of lectins and Mgat5 modified glycans, polylactosamine modified glycans, and/or glycoproteins that are associated with receptor clustering. When the lectin is a galectin the lattice is referred to as a "galectin-Mgat5 modified glycoprotein lattice". The stoichiometry of components of a lattice preferably provides optimal occupation of the lectin-glycan binding sites to create strong interactions among the components of the lattice resulting in an impediment to receptor clustering.

A lectin-Mgat5 modified glycan lattice, in particular a galectin-Mgat5 modified glycan lattice may restrict clustering of receptors on cell surfaces. By way of example, the galectin-Mgat modified glycan lattice may restrict TCR recruitment to the site of antigen presentation.

The invention also provides a peptide derived from the binding domain or binding site of a lectin (e.g. a carbohydrate recognition domain of a galectin) that interacts with a glycan component of a lectin-Mgat5 modified glycan lattice (e.g. a Mgat5 modified glycan, a polylactosamine modified glycan, or glycoprotein); or, an oligosaccharide derived from a Mgat5 modified glycan or polylactosamine modified glycan of a lectin-Mgat5 modified glycan lattice that interacts with one or more lectin, in particular a galectin. The peptide may preferably be derived from a carbohydrate recognition domain of a galectin.

The invention also relates to an oligosaccharide derived from a Mgat5 modified glycan or polylactosamine modified glycan, preferably of a T cell receptor, that interacts with one or more galectin.

By being "derived from" is meant any molecular entity which is identical or substantially equivalent to the native binding site of a molecule in a complex, or lattice of the invention (e.g. a lectin in particular, a galectin, or a glycan, in particular a Mgat5 modified glycan or polylactosamine modified glycan). A peptide or oligosaccharide derived from a specific binding site may encompass the amino acid or carbohydrate sequence of a naturally occurring binding site, any portion of that binding site, or other molecular entity that functions to bind to an associated or interacting molecule. A peptide or oligosaccharide derived from such a binding domain will interact directly or indirectly with an associated or interacting molecule in such a way as to mimic the native binding site. Such peptides and oligosaccharides may include competitive inhibitors, peptide mimetics, and the like.

The term "interact", "interacting", or "interaction" refers to a stable association between two molecules due to, for example, electrostatic, hydrophobic, ionic and/or hydrogen-bond interactions under physiological conditions.

"Peptide mimetics" are structures which serve as substitutes for peptides in interactions between molecules (See Morgan et al (1989), Ann. Reports Med. Chem. 24:243-252 for a review). Peptide mimetics include synthetic structures that may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide, or enhancer or inhibitor of the invention.

The invention also contemplates an altered glycan of a cell surface glycoprotein associated with receptor clustering resulting from the inhibition of a glycosyltransferase involved in the synthesis of the glycan. In an embodiment the altered glycan is an altered Mgat5 modified glycan or an altered polylactosamine modified glycan. By way of example, an altered Mgat5 modified glycan has a deficiency of β1-6 branches, and an altered polylactosamine modified glycan has a deficiency of N-acetyllactosamine or polylactosamine. An altered Mgat5 modified glycan or altered polylactosamine modified glycan cannot substantially interact or associate with a lectin, preferably a galectin.

Mgat5 modified glycans, polylactosoamine modified glycans and altered glycans may be assayed using substances that bind to the glycans. The substances that bind to the glycans may be antibodies or lectins. For example, leukoagglutinin (L-PHA) is a tetravalent plant lectin that binds specifically to Mgat5 modified glycans.

The invention contemplates antibodies specific for the complexes, lattice, peptides, oligosaccharides, and altered glycans of the invention. Antibodies include intact monoclonal or polyclonal antibodies, and immunologically active fragments (e.g. a Fab, (Fab)$_2$ fragment, or Fab expression library fragments and epitope-binding fragments thereof), an antibody heavy chain, and antibody light chain, a genetically engineered single chain Fv molecule (Ladner et al, U.S. Pat. No. 4,946,778), humanized antibodies, or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

Antibodies specific for a Mgat5 modified glycan, polylactosamine modified glycan, complex, lattice, or an altered glycan may be produced in Mgat5$^{-/-}$ mice using conventional methods.

Antibodies specific for the complexes, lattice, peptides, oligosaccharides, and altered glycans of the invention may be used to detect the complexes, lattice, etc. in tissues and to determine their tissue distribution. In vitro and in suit detection methods using the antibodies of the invention may be used to assist in the prognostic and/or diagnostic evaluation of disorders mediated by or involving receptor clustering, more particularly T cell receptor mediated disorders. Antibodies specific for the complexes, lattice, etc. of the invention may also be used therapeutically to modulate receptor clustering, more particularly T cell receptor clustering (i.e. T cell activation).

Evaluating Compounds that Regulate Receptor Clustering

The invention provides a method for evaluating a test compound for its ability to effect or regulate receptor clustering through glycans on cell surfaces (e.g. glycans of the receptor such as Mgat5 modified glycans or polylactosamine modified glycans). Changes to glycans on cell surfaces may increase or decrease receptor clustering thereby modifying signal transduction by the receptors.

"Receptor clustering" or "clustering of receptors" refers to the association of one or more receptor molecules on the surface of a cell to thereby initiate signal transduction, endocytosis, and other events in the cell. Receptor clustering may be initiated or induced by the interaction of ligands or anti-receptor antibodies with receptor molecules. Thus, in an aspect of the invention receptor clustering is ligand-dependent. Examples of receptor molecules include but are not limited to receptors that stimulate immune reactions (e.g. T cell receptors, Ig receptors, B cell receptors, and NK receptors), members of the HER family of transmembrane receptor tyrosine kinases [e.g. epidermal growth factor (EGF) receptor also known as HER1 or Erb1, HER (neu, Erb2), HER3 (Erb3), and HER4 (Erb4)], cadherin receptors (e.g. E-cadherin and N-cadherin), interleukin (IL) receptors including IL-2 receptor, TNFγ receptor, and integrins. In an embodiment, T cell receptor clustering is down regulated by a lectin-Mgat5 modifed glycan lattice which slows the migration of T cell receptors into clusters at the immune synapse. Dissociation of the lectin and glycan(s) of the lattice enhances T cell receptor clustering lowering the T cell activation threshold.

An aspect of the invention provides a method for evaluating a test compound for its ability to regulate receptor clustering through a lectin-Mgat5 modified glycan lattice, in particular a galectin-Mgat5 modified glycan lattice, or a component thereof.

Methods of the invention are designed to identify compounds or substances that affect receptor clustering particularly T cell receptor clustering (i.e. T cell activation). Novel substances are therefore contemplated that bind to or interact with molecules in a complex or lattice, or bind to other molecules that interact with the molecules in the complex or lattice, to compounds that interfere with, or enhance the interaction of the molecules in a complex or lattice, or other compounds that interact with the molecules. Therefore, by way of example, a compound may be a substance that binds to a lectin (e.g. galectin), a polylactosamine modified glycan, or a Mgat5 modified glycan; a molecule derived from a lectin (e.g. galectin), Mgat5 modified glycan, or polylactosamine modified glycan; or a substance which inhibits or enhances the interaction of a lectin (e.g. galectin) and a Mgat5 modified glycan or a polylactosamine modified glycan.

A compound that enhances or inhibits the interaction of a lectin (e.g. galectin) and a Mgat5 modified glycan or polylactosamine modified glycan is intended to include a peptide or peptide fragment derived from the binding site of a lectin (e.g. galectin), or oligosaccharide or fragment thereof derived from the binding site of the Mgat5 modified glycan or polylactosamine modified glycan. An enhancer or inhibitor will not include the full length sequence of the wild-type molecule. Peptide mimetics, oligosaccharide mimetics, and synthetic molecules with physical structures designed to mimic structural features of particular peptides or oligosaccharides, may serve as inhibitors or enhancers. Inhibitors or enhancers may affect receptor clustering, in particular T-cell receptor clustering. The enhancement or inhibition may be direct, or indirect, or b) a competitive or non-competitive mechanism.

The substances identified using the methods of the invention include but are not limited t peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), oligosaccharides, antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], and small organic or inorganic molecules. The substance or compound may be an endogenous physiological compound or it may be a natural or synthetic compound.

The invention particularly contemplates a method for evaluating a compound for its ability to modulate the biological activity of a complex or lattice of the invention, by assaying for an agonist or antagonist (i.e. enhancer or inhibitor) of the binding or interaction of molecules in the complex or lattice. The basic method for evaluating if a compound is an agonist or antagonist of the binding of molecules in a complex or lattice of the invention, is to prepare a reaction mixture containing the molecules and the substance under conditions which permit the formation of complexes or a lattice, in the presence of a test compound. The test compound may be initially added to the mixture, or may be added subsequent to the addition of molecules. Control reaction mixtures without the test compound or with a placebo are also prepared. The formation of complexes or a lattice is detected and the formation of complexes or a lattice in the control reaction but not in the reaction mixture indicates that the test compound interferes with the interaction of the molecules. The reactions may be carried out in the liquid phase or the molecules, or test compound may be imnnobilized as described herein.

It will be understood that the agonists and antagonists i.e. inhibitors and enhancers that can be assayed using the methods of the invention may act on one or more of the binding sites on the interacting molecules in the complex or lattice including agonist binding sites, competitive antagonist binding sites, non-competitive antagonist binding sites or allosteric sites.

The invention also makes it possible to screen for antagonists that inhibit the effects of an agonist of the interaction of molecules in a complex or lattice of the invention. Thus, the invention may be used to assay for a compound that competes for the same binding site of a molecule in a complex or lattice of the invention.

In an embodiment, the method comprises mixing a lectin-Mgat5 modified glycan lattice or a component thereof (e.g. lectin such as a galectin, a Mgat5 modified glycan, polylactosamine modified glycan), and a test compound under conditions which maintain the lattice or permit the formation of complexes between the lectin and one or more of the Mgat5 modified glycan, and polylactosamine modified glycan, and removing and/or detecting lectin-Mgat5 modified glycan lattice, complexes, lectin, Mgat5 modified glycan, or polylactosamine modified glycan. The invention also encompasses the compounds identified using this method of the invention.

Substances which modulate the activity of a complex or lattice of the invention can be identified based on their ability to bind to a molecule in a complex or lattice of the invention. Therefore, the invention also provides methods for identifying novel substances which bind molecules in a complex or lattice of the invention. Substances identified using the methods of the invention may be isolated, cloned and sequenced using conventional techniques.

Novel substances which can bind with a molecule in a complex or lattice of the invention may be identified by reacting one of the molecules with a test substance which potentially binds to the molecule, under conditions which permit the formation of substance-molecule conjugates and removing and/or detecting the conjugates. The conjugates can be detected by assaying for substance-molecule conjugates, for free substance, or for non-complexed molecules. Conditions which permit the formation of substance-molecule conjugates may be selected having regard to factors such as the nature and amounts of the substance and the molecule.

The substance-molecule conjugate, free substance or non-complexed molecules may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against the molecule or the substance, or labelled molecule, or a labelled substance may be utilized. The antibodies, proteins, or substances may be labelled with a detectable substance as described above.

A molecule, complex, or lattice of the invention, or a substance or compound used in a method of the invention may be insolubilized. For example, a molecule, complex etc. may be bound to a suitable carrier such as agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized molecule, complex etc. may be prepared by reacting the material with a suitable insoluble carrier using known chemical or physical methods, for example, cyanogen bromide coupling.

Compounds that bind to molecules of a complex or lattice of the invention or that interact with a molecule that binds to a molecule of a complex or lattice of the invention may be assayed by identifying protein-protein or protein-carbohydrate interactions using conventional methods such as co-immunoprecipitation, crosslinking and co-purification through gradients or chromatographic columns. Methods may also be employed that result in the simultaneous identification of genes which encode proteins interacting with a molecule. These methods include probing expression libraries with labeled molecules. Additionally, x-ray crystallographic studies may be used as a means of evaluating interactions with substances and molecules. For example, purified recombinant molecules in a complex of the invention when crystallized in a suitable form are amenable to detection of intra-molecular interactions by x-ray crystallography. Spectroscopy may also be used to detect interactions and in particular, Q-TOF instrumentation may be used. Two-hybrid systems may also be used to detect protein interactions ice vivo.

It will also be appreciated that the complexes or lattices of the invention may be reconstituted in vitro and the effect of a test substance may be evaluated in the reconstituted system.

The invention also contemplates cell based assays. In an aspect of the invention, a method is provided comprising (a) providing cells with receptors whereby clustering of the receptors is regulated through a lectin-Mgat5 modified glycan lattice or component thereof (e.g. lectin, Mgat5 modified glycans, and polylactosamine modified glycans); (b) mixing the cells, lectin, and a test compound, under conditions which permit the formation of a lectin-Mgat5 modified glycan lattice, complexes between a lectin and one or more glycan of the lattice, and/or receptor clustering; (c) detecting a lectin-Mgat5 modified glycan lattice, complexes, lectin, Mgat5 modified glycan, polylactosamine modified glycan, alterations to the lattice, complexes, lectin, Mgat5 modified glycan, or polylactosamine modified glycan, or detecting receptor clustering; and (d) comparing to a control to determine if the test compound potentially regulates receptor clustering.

In another aspect of the invention, a method is provided comprising (a) providing cells with receptors whereby clustering of the receptors is regulated through a lectin-Mgat5 modified glycan lattice or component thereof (e.g. lectin, Mgat5 modified glycans, and polylactosamine modified glycans); (b) mixing the cells, lectin, a test compound, and a ligand for the receptor that induces receptor clustering, under conditions which permit receptor clustering; (c) detecting receptor clustering; and (d) comparing to a control to determine if the test compound potentially regulates receptor clustering. The lattice on the cell surface may regulate the threshold cooperativity and dynamic range of ligand dependent responses.

In an embodiment of the invention a method is provided which comprises;
(a) mixing cells with T cell receptors comprising Mgat5 modified glycans or polylactosamine modified glycans, one or more galectin, and a test compound under conditions suitable for producing a galectin-Mgat5 modified glycan lattice;
(b) assaying for a galectin-Mgat5 modified glycan lattice; and
(c) comparing to a control in the absence of the test compound to determine if the test compound has the potential to regulate receptor clustering.

In an embodiment of the invention a method is provided which comprises;
(a) mixing cells with T cell receptors and Mgat5 modified glycans and/or polylactosamine modified glycans on their surface, one or more galectin, and a test compound under conditions suitable for producing receptor clustering of the T cell receptors;
(b) assaying for T cell receptor clustering or T cell signaling or activation;
(c) comparing to a control to determine if the test compound has the potential for regulating receptor clustering.

In a further embodiment of the invention, a method is providing for evaluating a test compound for its potential to regulate receptor clustering comprising:

(a) mixing cells with T cell receptors and Mgat5 modified glycans or polylactosamine modified glycans on their surface, one or more galectin, and a test compound under conditions suitable for producing a galectin-Mgat5 modified glycan lattice;
(b) assaying for Mgat5 modified glycans, polylactosamine modified glycans, galectin, or a galectin-Mgat5 modified glycan lattice, or alterations to the glycans or lattice;
(c) comparing to a control where an alteration to a Mgat5 modified glycan, polylactosamine modified glycan, galectin, or a galectin-Mgat5 modified glycan lattice, indicates that the test compound has potential to regulate receptor clustering.

In a still further embodiment of the invention, a method is providing for evaluating a test compound for its potential to regulate receptor clustering comprising:
(a) mixing Mgat5$^{-/-}$ T cells and a test compound under conditions suitable for clustering of T cell receptors on the T cells;
(b) assaying for T cell receptor clustering or T cell signaling; and
(c) comparing to a control to determine if the test compound has potential to regulate receptor clustering.

In a still further embodiment of the invention, a method is providing for evaluating a test compound for its potential to regulate receptor clustering comprising:
(a) mixing Mgat5$^{-/-}$ T cells, one or more galectin, and a test compound under conditions suitable for producing a galectin-Mgat5 modified glycan lattice;
(b) assaying for galectin-Mgat5 modified glycan lattice or T cell receptor clustering or T cell signaling; and
(c) comparing to a control to determine if the test compound has potential to regulate receptor clustering.

The methods for evaluating a test compound for potential to regulate T cell receptor clustering may include an antigen presenting cell, or a bead coated with an antigen or anti-TCR antibody may be used to induce or initiate T cell receptor clustering.

Mgat5 modified glycans, polylactosoamine modified glycans, and lectin-Mgat5 modified glycan lattices may be assayed in the methods of the invention using substances that bind to Mgat5 modified glycans, polylactosoamine modified glycans, or the lattices. The substances that bind to the glycans and lattices may be antibodies or lectins. For example, leukoagglutinin (L-PHA) may be used to assay for Mgat5 modified glycans.

T cell receptor clustering or T cell signaling or activation may be assayed using the methods illustrated herein and other standard methods known to a skilled artisan.

The invention contemplates methods for assaying for compounds and substances that regulate receptor clustering by modulating the activity of one or more enzyme involved in the biosynthesis of Mgat5 modified glycans or polylactosamine modified glycans, in particular a glycosyltransferase, more particularly Mgat5. Examples of methods for screening for substances that modulate the activity of such enzymes are illustrated herein for Mgat5. The invention also contemplates methods for screening for compounds and substances that modulate the amount of Mgat5 modified glycans or polylactosamine modified glycans.

Therefore, the invention provides methods for screening for substances having potential pharmaceutical utility in the treatment and diagnosis of conditions associated with increased or decreased receptor clustering, particularly T cell receptor clustering. In an embodiment of the invention a method of assaying for a therapeutic is provided comprising assaying for a substance that inhibits or stimulates the activity of Mgat5. Substances that inhibit or stimulate Mgat5 activity may be identified by reacting Mgat5 with an acceptor substrate and a sugar donor in the presence of a substance suspected of inhibiting Mgat5, under conditions whereby the Mgat5 is capable of transferring the sugar donor to the acceptor substrate to produce a sugar donor-acceptor substrate complex, and determining the effect of the substance by assaying for sugar donor-acceptor substrate complexes, unreacted Mgat5, unreacted sugar nucleotide donor or unreacted acceptor substrate.

Suitable acceptor substrates include a saccharide, oligosaccharides, polysaccharides, glycopeptides, glycoproteins, or glycolipids which are either synthetic with linkers at the reducing end or naturally occurring structures, for example, asialo-agalacto-fetuin glycopeptide. The sugar donor may be a nucleotide sugar, dolichol-phosphate-sugar or dolichol-pyrophosphate-oligosaccharide, for example, uridine diphospho-N-acetylglucosamine (UDP-GlcNAc), or derivatives or analogs thereof.

The Mgat5 may be obtained from commercial sources; it may be purified from immortalized cell lines such as small cell lung cancer cells such as QG (Gu, J. et al. J. Biochem. 113, 111-116, 1993); or prepared by expression of the gene encoding Mgat5 in host cells.

The acceptor substrate or sugar donor may be labeled with a detectable substance, and the interaction of the enzyme with the acceptor and sugar donor will give rise to a detectable change. The detectable change may be calorimetric, photometric, radiometric, potentiometric, etc. The activity of Mgat5 may also be determined using methods based on HPLC (Koenderman et al., FEBS Lett. 222:42, 1987) or methods employed synthetic oligosaccharide acceptors attached to hydrophobic aglycones (Palcic et al Glycoconjugate 5:49, 1988; and Pierce et al, Biochem. Biophys. Res. Comm. 146: 679, 1987).

The Mgat5 is reacted with the acceptor substrate and sugar donor at a pH and temperature and in the presence of a metal cofactor, usually a divalent cation like manganese, effective for the enzyme to transfer the sugar donor to the acceptor substrate, and where one of the components is labeled, to produce a detectable change. It is preferred to use a buffer with the acceptor substrate and sugar donor to maintain the pH within the pH range effective for the proteins. The buffer, acceptor substrate, and sugar donor may be used as an assay composition. Other compounds such as EDTA and detergents may be added to the assay composition.

Substances that inhibit or stimulate Mgat5 activity may also be assayed by treating immortalized cells that express Mgat5 with a substance suspected of inhibiting or stimulating Mgat5, and comparing the morphology of the cells with the morphology of the cells in the absence of the substance and/or with immortalized cells that do not express Mgat5.

Still further, a substance that inhibits or stimulates Mgat5 activity may also be identified by treating a cell that expresses Mgat5 with a substance that is suspected of affecting Mgat5 activity, and assaying for Mgat5-modified glycans or polylactosamine modified glycans on the surface of the cell. Mgat5-modified glycans and polylactosamine modified glycans can be measured using methods described herein and known in the art. For example, cells expressing Mgat5-modified glycans may be treated with a substance suspected of inhibiting or stimulating Mgat5-modified glycans. A lectin such as L-PHA is then added and the amount of binding can be compared to control cells which have not been treated with the substance and/or which do not express Mgat5-modified glycans.

In another method of the invention, immortalized cells expressing Mgat5-modified glycans may be treated with a substance suspected of inhibiting or stimulating Mgat5. The cells can be treated with a lectin such as L-PHA and the sensitivity to the lectin can be compared with controls cells which have not been treated with the substance and/or which do not express Mgat5. Examples of immortalized cells which can be used in the method are immortalized lung epithelial cell lines such as CHO cells, MvlLu cells, MDAY-D2 lymphoma, and lectin-resistant variants of these cell lines, which are transfected with a Mgat5 vector and MDCK cells. In the absence of an inhibitor the cells should show signs of morphologic transformation. In particular, morphologic transformation is evidenced by (a) fibroblastic morphology, spindle shape and pile up; (b) the cells are less adhesive to substratum; (c) there is less cell-cell contact in monolayer culture; (d) there is reduced growth-factor requirements for survival and proliferation; (e) the cells grow in soft-agar or other semisolid medium; (f) there is a lack of contact inhibition and increased apoptosis in low-serum high density cultures; (g) there is enhanced cell motility; and, (h) there is invasion into extracellular matrix and secretion of proteases. Substances which interfere with one or more of these phenotypes may be considered to inhibit Mgat5.

Substances which inhibit or stimulate transcription or translation of a gene encoding a glycosyltransferse in particular Mgat5 may be identified by transfecting a cell with an expression vector comprising a recombinant molecule containing a nucleic acid sequence encoding the glycosyltransferase (e.g. Mgat5), the necessary elements for the transcription or translation of the nucleic acid sequence and a reporter gene, in the presence of a substance suspected of inhibiting or stimulating transcription or translation of the gene encoding the glycosyltransferase (e.g. Mgat5), and comparing the level of expression of the glycosyltransferase (e.g. Mgat5) or the expression of the protein encoded by the reporter gene with a control cell transfected with the nucleic acid molecule in the absence of the substance. The method can be used to identify transcription and translation inhibitors or stimulators of the gene encoding the glycosyltransferase (e.g. Mgat5).

The nucleic acid molecule encoding the glycosyltransferase may be constructed having regard to the sequence of the glycosyltransferase gene (e.g. see Saito et al., 1994 supra for Mgat5 gene sequence) using chemical synthesis and enzymatic ligation reactions following procedures known in the art.

Suitable transcription and translation elements may be derived from a variety of sources, including bacterial, fungal, viral, mammalian, or insect genes. Selection of appropriate transcription and translation elements is dependent on the host cell chosen, and may be readily accomplished by one of ordinary skill in the art. Examples of such elements include: a transcriptional promoter and enhancer, an RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcription and translation elements may be Supplied by the native gene and/or its flanking sequences.

Examples of reporter genes are genes encoding a protein such as β-galactosidase (e.g. lac Z), chloramphenicol, acetyltransferase, firefly luciferase, or an immunoglobulin or portion thereof such as the Fc portion of an immunoglobulin preferably IgG. Transcription of the reporter gene is monitored by changes in the concentration of the reporter protein such as β-galactosidase, chloramphenicol acetyltransferase, or firefly luciferase. This makes it possible to visualize and assay for expression of recombinant molecules to determine the effect of a substance on expression of the glycosyltransferase (e.g. Mgat5) gene.

Mammalian cells suitable for carrying out the present invention include any malignant cells, for example, COS (e.g., ATCC No. CRL 1650 or 1651), BHK (e.g., ATCC No. CRL 6281), CHO (ATCC No. CCL 61), HeLa (e.g., ATCC No. CCL 2), and 293 (ATCC No. 1573). Suitable expression vectors for directing expression in mammalian cells generally include a promoter. Common promoters include SV40, MMTV, metallothionein-1, adenovirus Ela, CMV, immediate early, immunoglobulin heavy chain promoter and enhancer, and RSV-LTR.

Protocols for the transfection of mammalian cells are well known in the art and include calcium phosphate mediated electroporation, retroviral, and protoplast fusion-mediated transfection (see Sambrook et al., Molecular Cloning A Laboratory Manual, 2nd edition, Cold Spring Harbor Laboratory Press, 1989).

An agent that modulates Mgat5 activity, the amount of Mgat5 modified glycans, or the amount of binding of MgatV modified glycans and lectins (e.g. galectins) may comprise a complex of a lectin (e.g. galectin) associated with a Mgat5 modified glycan and/or a polylactosamine modified glycan, or a lectin-Mgat5 modified glycan lattice; a peptide derived from the binding domain of a lectin (e.g. galectin) that interacts with Mgat5 modified glycan or polylactosamine modified glycan; and/or an oligosaccharide derived from the Mgat5 modified glycan that interacts with a lectin (e.g. galectin).

The reagents suitable for applying the methods of the invention to evaluate substances and compounds that modulate receptor clustering, more particularly T cell receptor clustering, may be packaged into convenient kits providing the necessary materials packaged into suitable containers. The kits may also include suitable supports useful in performing the methods of the invention.

Regulating Receptor Clustering

The invention provides a method for regulating receptor clustering on cell surfaces comprising altering glycans on the cell surface associated with receptor clustering, in particular altering receptor glycosylation. Preferably the receptors are those that comprise Mgat5 modified glycans or polylactosamine modified glycans. Examples of receptors include receptors that stimulate immune reactions (e.g. T cell receptors, Ig receptors, B cell receptors, NK receptors), the HER family of transmembrane receptor tyrosine kinases [e.g. epidermal growth factor (EGF) receptor also known as HER1 or Erb1, HER2 (neu, Erb2), HER3 (Erb3), and HER4 (Erb4)], cadherin receptors (e.g. E-cadherin and N-cadherin), interleukin (IL) receptors including IL-2 receptor, TNFγ receptor, and integrins.

Glycosylation may be altered by modulating one or more glycosyltransferase enzyme involved in the synthesis of glycans involved in receptor clustering, in particular N-glycans and N-glycan intermediates (e.g. Mgat5 modified glycans or polylactosamine modified glycans). Altering glycosylation may involve increasing or decreasing Mgat5 modified glycans or polylactosamine modified glycans associated with receptor clustering. In a preferred embodiment, an enzyme involved in the synthesis of the glycans is modulated (e.g. Mgat5).

In accordance with a particular aspect, the present invention relates to a method for regulating receptor clustering on cell surfaces, in particular ligand-dependent receptor clustering, more particularly T cell receptor clustering comprising modulating Mgat5 activity, the amount of Mgat5 modified glycans, polylactosamine modified glycans, or lectin-Mgat5 modified glycan lattice, or the amount of binding or interaction of one or more of MgatV modified glycans or polylactosamine modified glycans and lectins that interact with the glycans (e.g. galectins).

Receptor clustering or oligomerization, in particular ligand-dependent receptor clustering, may be reduced or inhibited by increasing the amount or levels of Mgat5 modified glycans, polylactosamine modified glycans, and/or lectin-Mgat5 modified glycan lattice, increasing the activity or amount of one or more glycosyltransferase enzyme, or enhancing the interaction between glycans involved in receptor clustering and substances that bind to the glycans that regulate receptor clustering (e.g. lectins).

Receptor clustering, in particular ligand-dependent receptor clustering, may be enhanced or increased and glycosylation of the receptor may be altered by decreasing the amount or levels of Mgat5 modified glycans, polylactosamine modified glycans, and/or lectin-Mgat5 modified glycan lattice, decreasing the activity or amount of one or more glycosyltransferase enzyme, or inhibiting the interaction between glycans involved in receptor clustering and substances that bind to the glycans that regulate receptor clustering.

In an aspect of the invention a method is provided for lowering T cell activation threshold to agonists comprising decreasing Mgat5 modified glycans, polylactosamine modified glycans, or galectin-Mgat5 modified glycan lattice on the surface of the cells, or dissociating galectin from such glycans or lattice thereby lowering the T cell activation threshold. Mgat5 modified glycans, polylactosamine modified glycans, or galectin-Mgat5 modified glycan lattice on the surface of the cells may be decreased by inhibiting a glycosyltransferase such as Mgat5.

In another aspect, a method is provided for restricting T cell receptor recruitment in response to an agonist or increasing T cell activation threshold comprising increasing Mgat5 modified glycans, polylactosamine modified glycans, or galectin-Mgat5 modified glycan lattice on the surface of the T cells, or enhancing the interaction between one or more components of a galectin-Mgat5 modified glycan lattice (e.g. a galectin and glycans of the lattice) thereby increasing the T cell activation threshold. The amount of glycans or lattice on the surface of the cells may be increased by increasing the levels or activity of one or more glycosyltransferase enzyme (e.g. Mgat5).

In accordance with another aspect of the invention, a method is provided for treating or preventing a condition associated with decreased or increased receptor clustering or a receptor clustering defect in a subject comprising altering glycans associated with or involved in receptor clustering. Glycans can be altered or modified by modulating a glycosyltransferase enzyme involved in the synthesis of the glycans.

In accordance with a particular aspect of the invention, a method is provided for treating or preventing a condition associated with decreased or increased receptor clustering, more particularly T cell receptor clustering, comprising modulating Mgat5 activity, the amount of Mgat5 modified glycans, polylactosamine modified glycans, and/or lectin-Mgat5 modified glycan lattice, and/or the amount of binding or interaction of one or more MgatV modified glycans, polylactosamine modified glycans and lectins e.g. galectins.

A receptor clustering defect may be involved in conditions such as autoimmune diseases or proliferative disorders such as cancer.

A condition associated with increased T cell receptor clustering may include a T cell mediated autoimmune disease such as insulin-dependent diabetes mellitus, multiple sclerosis, rheumatoid arthritis, myasthenia gravis, systemic lupus erythematosus, autoimmune hemolytic anemia, glomerulonephritis, enhanced delayed type hypersensitivity, allergic conditions, hypersensitivity, and autoimmune encephalomyelitis. Conversely, T cell recognition of cancers and immune therapy of cancer is limited by weak stimulation of T cells by tumor cells. The present invention may also be used to treat cancers susceptible to immune modulation.

In an aspect the invention contemplates a method for treating or preventing an autoimmune disease in a subject comprising reducing T cell receptor clustering in the subject T cell receptor clustering is reduced by increasing the amount of Mgat5 modified glycans, polylactosamine modified glycans, and/or lectin-Mgat5 modified glycan lattice on the surface of T cells of the subject In an embodiment, the method comprises up regulating or increasing the amount of Mgat5.

In an aspect the invention contemplates a method for treating or preventing cancer in a subject comprising increasing T cell receptor clustering in the subject T cell receptor clustering is increased by decreasing the amount of Mgat5 modified glycans, polylactosamine modified glycans, and/or lectin-Mgat5 modified glycan lattice on the surface of T cells of the subject. In an embodiment, the method comprises down regulating or decreasing the amount of Mgat5.

In an embodiment of the invention, a method is provided for treating or preventing a condition associated with a growth factor receptor, in particular epidermal growth factor receptor, comprising regulating clustering or oligomerization (e.g. dimerization) of the growth factor receptor by altering glycosylation of the receptor, modulating Mgat5 activity, the amount of MgatV modified glycans, polylactosamine modified glycans, and/or the binding of MgatV modified glycans or polylactosamine modified glycans and lectins for the glycans. Inhibition of growth factor receptor clustering may be useful in treating conditions involving aberrant grouch factors including but not limited to cancers such as solid human cancers, NSCL, breast cancer, head and neck cancer, gastric cancer, prostate cancer, bladder cancer, ovarian cancer, colorectal cancer, gliobastomas, and renal cell carcinoma One or more agents may be used to regulate receptor clustering. In particular, one or more agents may be used to modulate glycosyltransferase activity, more particularly Mgat5 activity, the amount of Mgat5 modified glycans or polylactosamine glycans, the amount of binding of MgatV modified glycans or polylactosamine modified glycans and lectins that interact with the glycans (e.g. galectins), or the amount of lectin-Mgat5 modified glycan lattice.

Agents that modulate glycosyltransferase activity, more particularly Mgat5 activity, include known inhibitors or enhancers of glycosyltransferases, compounds or substances identified using the methods described herein, nucleic acids encoding the glycosyltransferases, and antisense sequences of the nucleic acid sequence encoding the glycosyltransferases. Examples of glycosyltransferase inhibitors and enhancers are illustrated herein for Mgat5.

By way of example, known inhibitors of Mgat5 include an analog of the acceptor substrate for Mgat5, βGlcNAc (1,2) αMan(1,6)βManOR, where the reactive 6'OH group has been removed (Palcic, M. M. et al., J. Biol. Chem. 265 (12) 6759-6769). Inhibitors of enzymes earlier on in the Golgi oligosaccharide processing pathway may also be used to inhibit Mgat5 activity. Examples of inhibitors of other enzymes in the Golgi oligosaccharide processing pathway include mannosidase inhibitors such as swainsonine, 1,5-dideoxy-1,5-imino-5-mannitol and 1,4-dideoxy-1,4imino-D-mannitol.

Recombinant molecules containing the nucleic acid sequence Mgat5 in an antisense orientation may be used to inhibit Mgat5 activity. The nucleic acid sequence shown in Saito, H. et al. Biochem. Biophys. Res. Comm. 198;318-327, 1994, or parts thereof, may be inverted relative to their normal presentation for transcription to produce antisense nucleic acid molecules. The antisense nucleic acid molecules may be constructed using chemical synthesis and enzymatic ligation reactions using procedures known in the art. The antisense nucleic acid molecules or parts thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The amount of Mgat5 modified glycans may be increased in cells by administering Mgat5, a nucleic acid molecule encoding Mgat5, an agent that stimulates Mgat5, or a complex of the invention. Increased cell surface Mgat5 modified glycans may enhance the lectin-Mgat5 modified glycan lattice (e.g. galectin-Mgat5 modified glycan lattice) at the cell surface so as to restrict receptor clustering (e.g. T cell receptor clustering). The amount of polylactosoamine modified glycans may be increased in cells by administering one or more enzyme necessary for the production of the glycans, a nucleic acid molecule encoding the enzyme, an agent that stimulates the enzyme, or a complex of the invention. Increased cell surface polylactosamine modified glycans may enhance the lectin-Mgat5 modified glycan lattice (e.g. galectin-Mgat5 modified glycan lattice) at the cell surface so as to restrict receptor clustering (e.g. T cell receptor clustering). These approaches may be useful in the prevention and treatment of T cell mediated autoimmune diseases.

Agents, compounds, and substances described herein or identified using a method of the invention may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa, USA 1985). On this basis, the compositions include, albeit not exclusively, solutions of the substances or compounds in association with one or more pharmaceutically acceptable vehicles or diluents, and contained in buffered solutions with a suitable pH and iso-osmotic with the physiological fluids.

The activity of a pharmaceutical composition, an agent, compound, or substance described herein or identified using a method described herein may be confirmed in animal experimental model systems.

In accordance with an aspect of the invention there is provided a method of, and products for, diagnosing and monitoring conditions characterized by an abnormality in receptor clustering comprising assaying for differential glycosylation of the receptor. Differential glycosylation may be assayed by determining the presence of Mgat5 modified glycans, polylactosamine modified glycans, lectin-Mgat5 modified glycan lattice, or an alteration or change in such glycans or lattice, compared to a control.

In an embodiment, a method of, and products for, diagnosing and monitoring conditions characterized by an abnormality or defect of receptor clustering involving the interaction of a galectin and Mgat5 modified glycan or polylactosamine modified glycan is provided comprising determining the presence of one or more of a complex of the invention, a Mgat5 modified glycan, a polylactosamine modified glycan, a galectin-Mgat5 modified glycan lattice, or one or more of an altered Mgat5 modified glycan, polylactosamine modified glycan, or a galectin-Mgat5 modified glycan lattice.

Nucleic acid molecules encoding MgatV, an Mgat5 polypeptide, and antibodies specific for Mgat5, complexes, lattice, oligosaccharides, or peptides of the invention may be used in the prognostic and diagnostic evaluation of conditions associated with increased or decreased receptor clustering more particularly T cell receptor clustering, and the identification of subjects with a predisposition to such conditions. In an embodiment, the nucleic acid molecules, Mgat5, and antibodies may be used in the diagnosis and staging of T cell mediated autoimmune diseases.

The following non-limiting example is illustrative of the present invention.

EXAMPLE

Methods

Delayed-type hypersensitivity (DTH) skin reaction: To induce delayed-type hypersensitivity, 100 µl of 5% (w/v) 4-ethoxymethilene-2-phenyl-2-oxazolin-5-one (oxazolone) (Sigma) in ethanol/acetone (3:1, v/v) was injected epicutaneously to the shaved backs of the 129/sv mice. Four days after sensitization, 25 µl of 1%, (w/v) oxazolone was applied on each side of the right ear, and the left ear received 25 µl of olive oil/acetone on each side. Ear swelling was measured with a micrometer at 24 h intervals for the next 5 days, and swelling was reported as the difference between the ear thickness of the right minus the left ears.

EAE model: Mice (129/sv) 8-12 weeks of age were injected subcutaneously with 100 Ill of rabbit MBP (Sigma) emulsified 1:1 with complete Freunds adjuvant at three different total doses (25, 100 and 500 µg/mouse). Mice were observed from day 5 to day 50, and observations were done blinded with respect to the genotype until day 36. For lower doses of 25 and 50 µg/mouse, half the total was injected on day 0 in the right flank and the other half on day 7 in the left flank. The high dose of 500 µg/mouse was injected all on day 0 at the base of the tail, and 500 µg of pertussis toxin was injected via the tail vein on day 0 and day 2.

T cell proliferation: Naive T-cells were purified from spleens of 8-12 week old mice by negative selection using CD3+T cell purification columns (R&D laboratories) or by panning on plates pre-coated with anti-CD19 antibody (Pharmingen). T cell proliferation was measured by culturing cells for 48 h in RPMI, 10% FCS, $10^{-5}$ M 2-mercaptoethanol in the presence of one or more of the following soluble antibodies: hamster anti-mouse CD3ε (clone 2C11; Cedarlane), hamster anti-mouse TCRα/β (clone H59.72; Pharmingen) or 0.5 µg/ml anti-mouse CD-28 (Pharmingen). PMA at 10 ng/ml and ionomycin at 0.5 µg/ml were also used to stimulate cells. Two µCi of $^3$H-thymidine were added for the last 20 h of incubation, and cells were harvested on fiberglass filters and radioactivity was measured in a β-counter.

TCR clustering: Six-micron polystyrene beads (Polysciences) in PBS were coated with hamster anti-mouse CD3ε antibody (Clone 2C11; Cederlane) at 2 µg/ml antibody followed by coating with 200 µg/ml bovine serum albumin (BSA). To measure TCR clustering, $5 \times 10^4$ T cells were incubated with $2.5 \times 10^5$ anti-CD3ε antibody-coated beads in 100 µl RPMI 1640+10% FCS at 37° C. for 10 minutes placed on poly-L-lysine coated cover slips. The cells were fixed with 10% formalin, stained with 2 µg/ml fluorescein isothiocyanate (FITC) labeled anti-TCRα/β antibody (Pharmigen), solubilized with 0.2% Triton X-100, labelled with rhodamine-phalloidin and Hoechst, and then visualized by deconvolution microscopy. For disaccharide competition, wild type T cells were incubated for 20 min with 0, 0.01, 0.03, 0.09, 0.27, 0.8, and 2.4 mM of disaccharide prior to exposure to anti-CD3ε antibody beads. To measure TCR internalization, purified splenic T cells stimulated with either 0.1 µg/ml$^{-1}$ anti-CD3 antibody or with 10 ng/ml PMA for varying lengths of time were harvested and stained with FITC-anti-TCRα/β. PMA concentrations were not limiting as 10, 50 and 100 ng/ml produced similar internalization and cell activation results. To measure actin reorganization, purified splenic T cells, stimulated with 0.1 µg/ml$^{-1}$ anti-CD3 for varying lengths of time, were fixed with 4% paraformaldehyde for 10 minutes, washed with PBS and stained with rhodamine-phalloidin and mean fluorescence intensity (MFI) was determined by FACS.

TCR signaling: T cells ($1 \times 10^6$) and anti-CD3ε antibody coated beads ($5 \times 10^6$ at 0.4 µg/ml antibody) in 100 µl RPMI 1640 were pelleted, incubated at 37° C. for various times, then solublized with ice cold 50 mM Tris pH 7.2, 300 mM NaCl, 0.5% Triton X-100, protease inhibitor cocktail (Boeringer Mannheim) and 2 mM orthovanadate. Zap-70 was immunoprecipitated by incubating whole cell lysates with rabbit polyclonal anti-Zap-70 agarose conjugate (Santa Cruz) overnight at 4° C., followed by one wash with lysis buffer and 3 washes with PBS. Western blotting was done with whole cell lysates or immunoprecipitates separated on SDS-PAGE gels under reducing conditions, transferred electrophoretically onto PVDF membranes and immunoblotted with antibodies to Akt/PKB (NEB), phospho-Akt/PKB (NEB), phosphotyrosine (clone 4G10, Upstate Biotechnology), Zap 70 (clone Zap70-6F7, Zymed), TCRα (polyclonal, Santa cruz) and rabbit anti-galectin-3 (Dr. A Raz, University of Michigan). Cell surface proteins were biotinylated using sulfosuccininmidobiotin (NHS-biotin) for 30 min, PBS pH 8.0. Cells were lysed and labeled protein was captured on streptoavidin-agarose beads. To cross-link surface proteins on purified naive T cells, the homobifunctional cross-linker dithiobis (sulfosuccinimydylpropionate (DTSSP) was used at 0.1 mg/ml with $10^6$ cell/ml in PBS pH 8.0 for 10 min at 20° C. T cells were preincubated for 20 min with or without 2 mM lactose, and reacted with DTSSP in the presence of the same. Aliquots of cell lysate were immunoprecipitated with rabbit anti-galectin-3 antibody or non-immune rabbit serum (NS), separated on reducing— SDS-PAGE and Western blotted for CD3ε and TCRα chain. The band above CD3ε is cross-reactivity of secondary antibody with light-chain.

To measure $Ca^{++}$ mobilization, purified T cells were loaded with 10 μM AM ester of Fluo-3 (Molecular Probes) washed and stimulated with 10 μg/ml of anti-CD3ε antibody at 37° C. Emission at 525 nm was taken using a spectrofluorimeter with excitation at 488 nm. Data is plotted as a fraction of the $Ca^{++}$ mobilized by addition of 2 $\mu g/ml^{-1}$ of ionomycin. LacZ activity in Mgat5$^{-/-}$ T cells was detected by loading cells with flourescin-di-β-D-galactopyranoside (FDG) (Molecular Probes) at 10° C., and allowing the reaction to proceed for 30 min. The reaction was stopped by the addition of 1 mM phenyl-β-thiogalactoside.

Results and Discussion

To explore the role of Mgat5 in T cell immunity, Mgat5-deficient mice were examined for evidence of immune dysfunction. Mgat5$^{-/-}$ mice are born healthy, and lack Mgat5 N-glycan products in all tissues examined (16). At 3 months of age, peripheral white blood cells, erythrocyte and serum levels of IgM and IgG were comparable in Mgat5$^{-/-}$, Mgat5$^{+/-}$ and Mgat5$^{+/+}$ mice (data not shown). The CD4 and CD8 reactive T cell populations in the spleen and thymus were also in the normal range (FIGS. 1B,C). At 12-20 months of age, an increased incidence of leukocyte colonies in kidney and enlarged spleens were observed in Mgat5$^{-/-}$ mice. Furthermore, 32% of the Mgat5$^{-/-}$ (6/19 mice) had macroscopic hematuria, mononuclear infiltrates and extensive accumulation of fibrin within Bowman's space (crescents), characteristic of proliferative glomerulonephritis (FIG. 1D). This form of renal injury is often observed in autoimmune mediated glomerulonephritis. Milder renal defects were observed in 68% of the Mgat5$^{-/-}$ mice but not in the Mgat5$^{+/-}$ or Mgat5$^{+/+}$ mice (0/19).

To examine T cell responses in the mice, a type IV delayed-type hypersensitivity (DTH) reaction was induced and tissue swelling was measured. The protein-reactive hapten oxazolone was applied topically to the backs of the mice, then again 4 days later to the right ear. Ear swelling in Mgat5$^{+/+}$ mice peaked 24 hours post application, and swelling was completely gone by day 5. Ear swelling in Mgat5$^{-/-}$ mice attained a higher maximum between 48 and 72 h, and persisted for a longer time (FIG. 1E). To study T cell dependent autoimmunity in vivo (17), experimental autoimmune encephalomyelitis (EAE) was induced by immunizing mice with myelin basic protein (MBP) at 3 doses: 25, 100 and 500 μg/mouse. At the lowest dose of MBP, 25 μg/mouse, the incidence of EAE was significantly greater in Mgat5 deficient mice. Furthermore, 25 and 100 μg/mouse doses of MBP produced more severe EAE in Mgat5$^{-/-}$ mice compared to wild type littermates, characterized by an earlier onset, greater motor weakness and more days with disease (Table 1). Myelin injections of 500 μg/mouse induced disease in all mice with greater peak scores and no significant differences in disease incidence or severity between genotypes. These results indicate that mice lacking Mgat5-modified glycans are more susceptible to DTH and EAE autoimmune disease.

Figure 2:
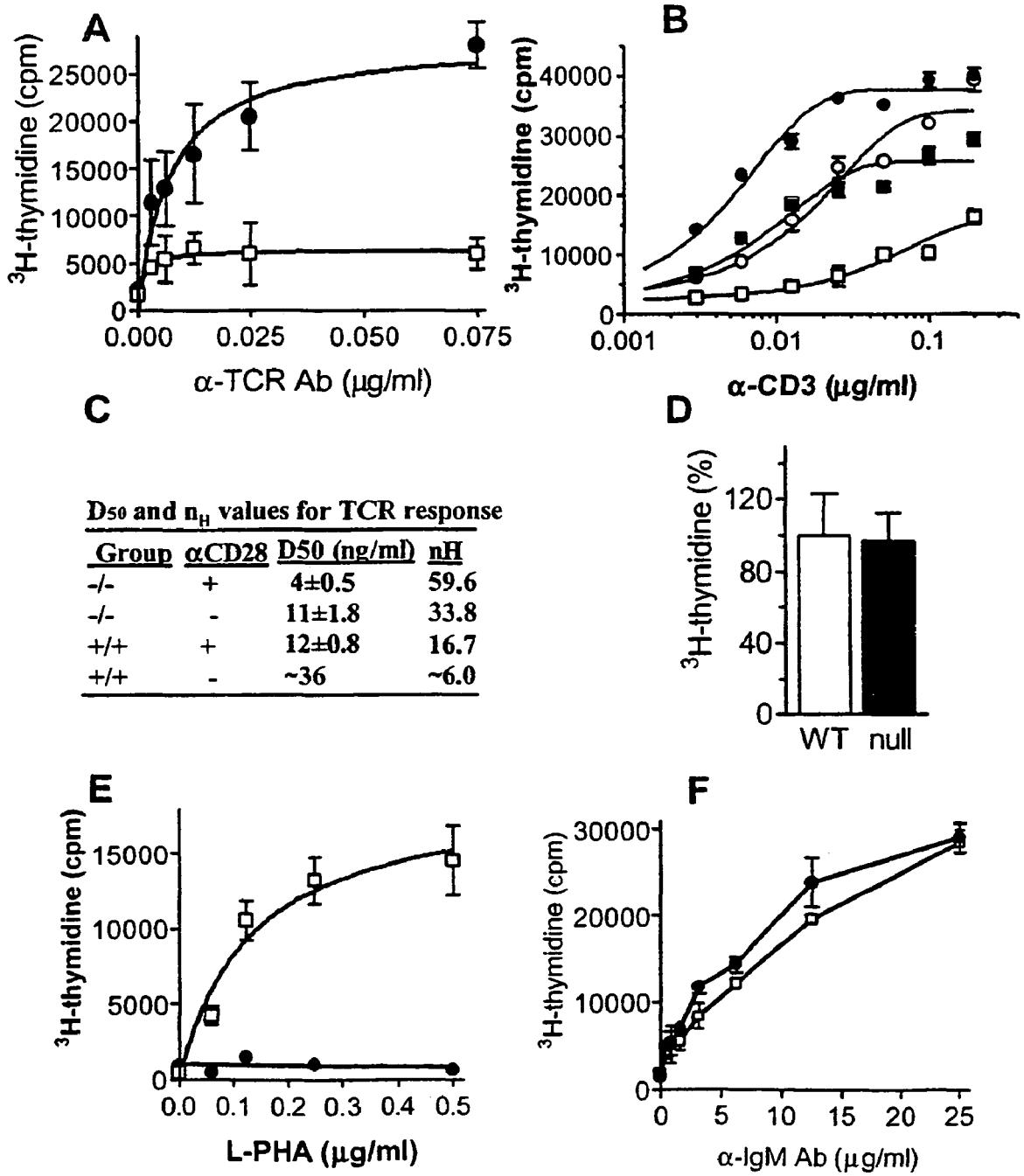
FIG. 2 Mgat5$^{-/-}$ T cells are hypersensitive to TCR agonists. (A) Spleen cells were cultured with anti TCRα/β antibodies for 48 h. Filled circles, Mgat5$^{-/-}$; open squares, Mgat5$^{+/+}$. (B) Purified T cells from spleen were stimulated for 48 h with anti-CD3ε antibody in the absence (○,□) or presence (●,■) of anti-CD28 antibody; Mgat5$^{-/-}$ (circles) and Mgat5$^{+/+}$ (squares) cells. (C) The Hill slope ($n_H$) of the sigmodal curves was calculated using $Y=x^{nH}/(k^{nH}+x^{nH})$. (D) Stimulation of splenic T cells with PMA plus ionomycin for 48 h. (E) Stimulation of splenic T cells from Mgat5$^{-/-}$ (●) and Mgat5$^{-/+}$ (□) mice with L-PHA and (F) Stimulation of splenic B cells with anti-IgM antibody for 48 h. The means±SD of triplicate determinations were graphed.

In vitro, splenic T cells from Magt5–/– mice hyperproliferated in response to anti-TCRα/β antibody (FIG. 2A). To examine this hypersensitivity in more detail, purified ex vivo T cells were cultured at low density and stimulated with increasing concentrations of soluble anti-CD3ε antibody in the presence or absence of anti-CD28 antibody (FIG. 2B). Both the Mgat5 deficiency and CD28 engagement reduced the requirements for TCR agonist as indicated by $D_{50}$ values and were additive when combined (FIG. 2C). Furthermore, the apparent Hill coefficient ($n_H$), a measure of synchrony in the responding cell population, was increased by both the Mgat5 deficiency and by CD28 engagement Therefore, the stimulatory effects of the Mgat5 mutation and CD28 co-receptor engagement were additive and similar in potency.

Alterations in cell surface TCR complex levels and intracellular signaling potential of T cells were examined and ruled-out as possible causes of the Mgat5$^{-/-}$ hypersensitivity. The Mgat5 deficiency did not significantly alter cell surface expression of CD3, CD4, CD8, TCRα/β, CD28 or CTLA-4 glycoproteins in resting T cells (FIGS. 1B, C and data not shown). Intracellular signaling potential in Mgat5$^{-/-}$ T cells is normal, as treatment with the phorbol ester PMA and the $Ca^{++}$ ionophore ionomycin stimulated T cells equally well from mice of both genotypes (FIG. 2D).

The relationship between cell surface Mgat5-modified glycans and T cell activation was examined. Leukoagglutinin (L-PHA) is a tetravalent plant lectin and commonly used T cell mitogen that binds specifically to Mgat5-modified glycans. Mgat5$^{-/-}$ T cells were completely unresponsive to L-PHA, confirming that Mgat5-modified glycans are required for stimulation by this lectin (FIG. 2E). L-PHA reactive N-glycans are also present on B cells, but L-PHA is not a B cell mitogen. Furthermore, B cell responses to anti-IgM antibody, LPS and IL-4 plus anti-CD40 antibody were similar for cells from Mgat5$^{-/-}$ and Mgat5$^{+/+}$ mice (FIG. 2F and data not shown). In T cells, L-PHA induces signaling common to TCR engagement, including phosphorylation of CD3ζ, $Ca^{++}$ mobilization, PKC-γ and Ras/mitogen-activated protein kinase (Mapk) activation (18; 19). The TCRα/β chains have 7 N-glycans in total, and some are branched complex-type structures with L-PHA reactivity (20; 21). These data indicate that Mgat5-modified glycans are present on glycoproteins of the TCR complex and required for L-PHA mitogenesis.

Figure 3:
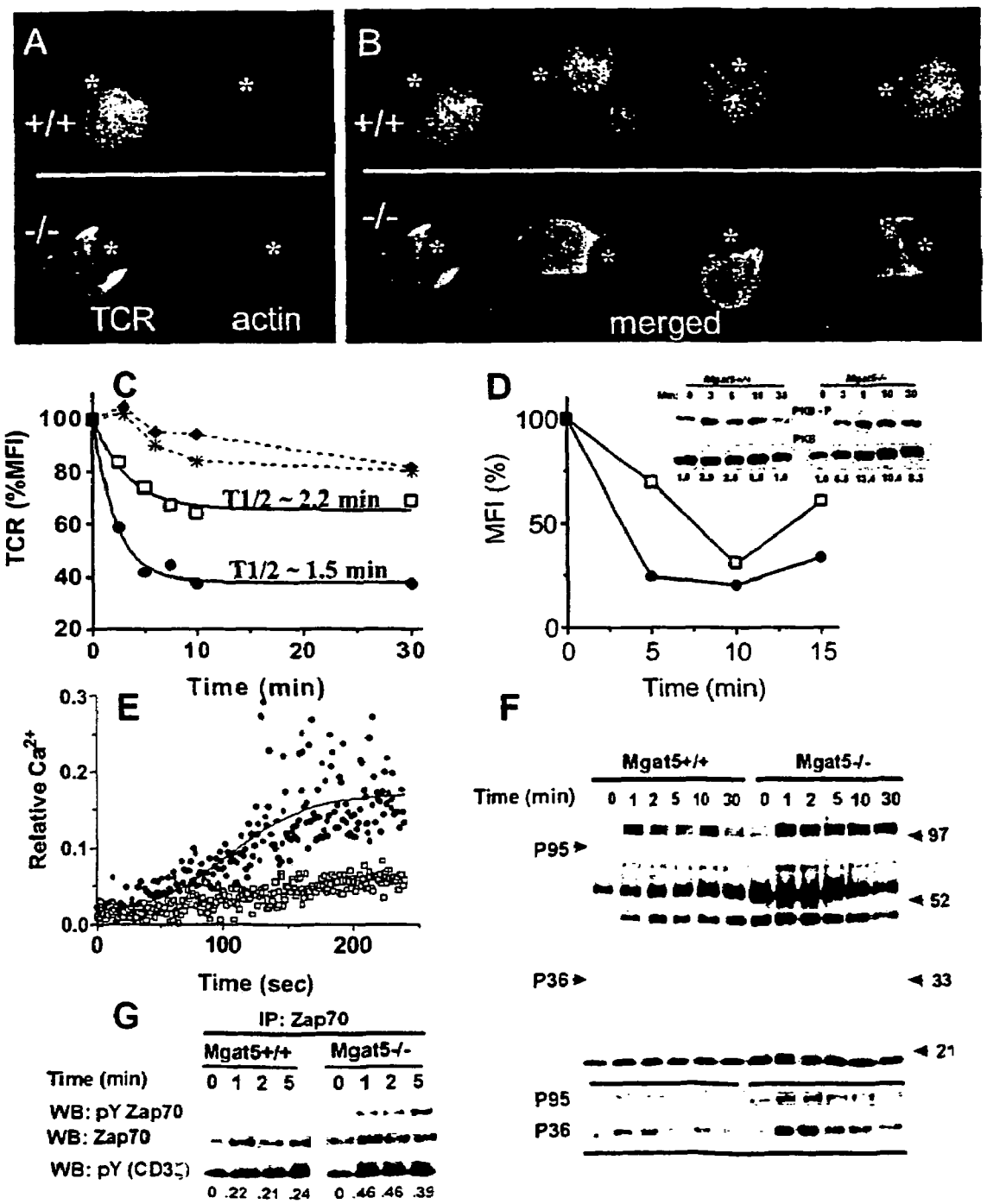
FIG. 3 TCR clustering, actin reorganization and signaling in T cells from Mgat5$^{-/-}$ and Mgat5$^{+/+}$ mice. (A) TCR and actin microfilament distribution in T cells stimulated by anti-CD3ε coated beads. (B) Merged images of Mgat5$^{-/-}$ and Mgat5$^{+/+}$ cells. Clustering was observed in 5/6 and 0/6 randomly photographed cells, respectively. (C) TCR internalization was monitored by FACS analysis using FITC-anti-TCR$_{α/β}$ antibodies to measure cell surface TCR remaining at various times after the addition of anti-CD3ε antibody. Changes in mean fluorescence intensity (MFI) with time are graphed. T cells from Mgat5$^{-/-}$ (●,♦) or Mgat5$^{+/+}$ (□,*) mice were treated with anti-CD3ε antibody (●,□); or with PMA (♦,* ). Similar results were obtained when the stimulation and detection roles of anti-TCR$_{α/β}$ and anti-CD3 were reversed. (D) Actin polymer content in T cells from Mgat5$^{-/-}$ (●), or Mgat5$^{+/+}$ (□) mice at times after stimulation with anti-CD3ε antibody, measured by FACS. Western blot for phospho-Akt/PKB in T cell lysates following addition of anti-CDε antibody is shown. The values below are fold increase in PKB-P normalized to PKB protein. (E) Ca$^{2+}$ mobilization in purified T cells from Mgat5$^{-/-}$ (≡), and Mgat5$^{+/+}$ (□) mice stimulated with anti-CD3ε antibody. (F) Western blot with anti-phosphotyrosine antibody detecting phosphorylated proteins in T cells lysates after incubation with anti-CD3ε antibody coated beads for various times. A longer exposure was used to reveal bands (arrowheads at left) migrating as p95 and p36 shown below. Arrows at the right indicate the positions of molecular mass markers. (G) Immunoprecipitation of Zap70 and Western blotting for phosphotyrosine (pY) to detect Zap70 and CD3ζ (values below are CD3ζ ratio P23/P21).

When bound to major histocompatibility complex (MHC)/peptide, TCRs cluster with an inherent affinity greater than unligated TCR and the stability of these clusters is critical for intracellular signaling (22). However, the density of TCRs measured at the site of T cell-APC (antigen-presenting cell) contact is only marginally increased relative to the remaining cell surface, leaving the majority of the TCRs unengaged by MHC/peptide (4). It is possible that ligand induced TCR clustering in the plane of the membrane may be increased in the absence of Mgat5-modified glycans, thus lowering Mgat5$^{-/-}$ T-cell activation thresholds. To visualize TCR reorganization in response to an antigen-presenting surface, polystyrene beads were coated with anti-CD3ε antibody and incubated with purified ex vivo T cells. After 10 minutes of contact, TCRs in Mgat5$^{-/-}$ cells was markedly more concentrated at the bead surface compared to Mgat5$^{+/+}$ cells (FIGS. 3A, B). TCRs on wild type cells could not be induced to cluster to the same extent as Mgat5$^{-/-}$ cells even with longer incubations (20 min) or using anti-CD3ε plus anti-CD28 coated beads (data not shown). Actin microfilaments were more concentrated at the bead contact site in Mgat5$^{-/-}$ cells, and overlapped more extensively with TCR in the merged images compared to Mgat5$^{+/+}$ T cells (FIGS. 3A, B). TCRs are internalized following productive TCR clustering (1), and this was significantly greater in Mgat5$^{-/-}$ compared to Mgat5$^{+/+}$ cells (FIG. 3C, solid lines). Intracellular signaling mediated by PMA treatment induces TCR internalization but at similar rates in Mgat5$^{-/-}$ and Mgat5$^{+/+}$ cells (FIG. 3C, dotted lines). Microfilament re-organization was more rapid in Mgat5 deficient T cells following soluble anti-CD3ε antibody stimulation (FIG. 3D). Akt/protein kinase B (PKB) phosphorylation is dependent upon phosphoinositide 3-OH kinase activity, which stimulates Rac/CDC42 GTPases and actin filament re-organization (23). Phosphorylated Akt/PKB displayed a greater fold increase in Mgat5$^{-/-}$ compared to Mgat5$^{+/+}$ T cells (FIG. 3D). Mobilization of intracellular Ca$^{2+}$ following stimulation with soluble anti-CD3ε antibody was enhanced in the absence of Mgat5-modified glycans (FIG. 3E). Tyrosine phosphorylation of multiple proteins was increased and persisted longer in Mgat5$^{-/-}$ T cells exposed to anti-CD3ε antibody coated beads. (FIG. 3F). Immunoprecipitation of Zap70 revealed increased phosphorylation in Mgat5 /cells 1 to 5 min following stimulation. Zap70 kinase binds to dual phosphorylated immunoreceptor tyrosine-based activation motif domains of CD3ζ, and association of the latter with Zap70 was increased in Mgat5$^{-/-}$ compared to Mgat5$^{+/+}$ T cells (FIG. 3G). In summary, the Mgat5 deficiency enhanced ligand-dependent TCR aggregation, and consequently, signal transduction and microfilament re-organization.

Figure 4:
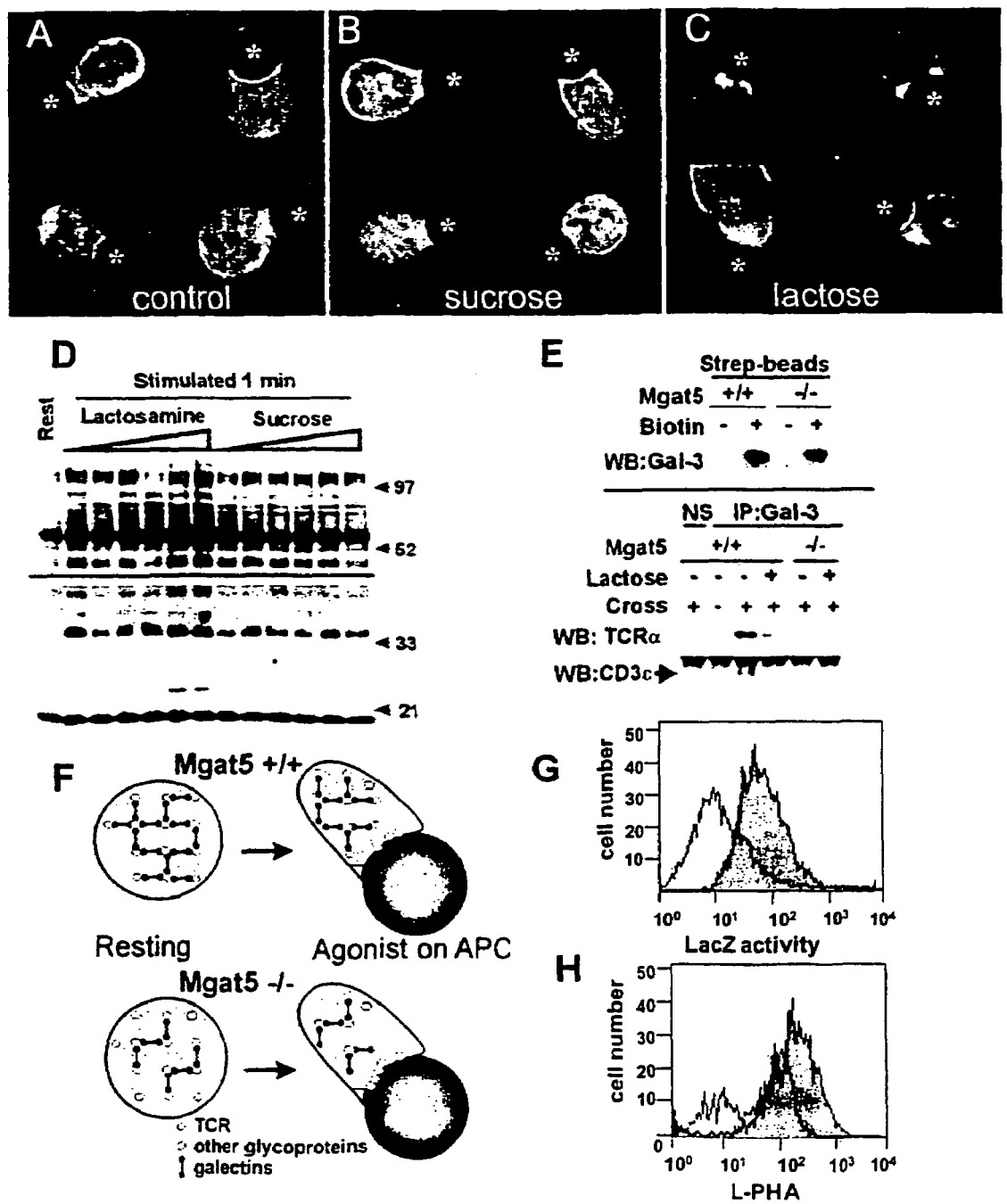
FIG. 4 Lactose stimulates TCR aggregation and signaling in Mgat5$^{+/+}$. Purified T cells pre-incubated for 20 min with buffer (A), 2 mM sucrose (B), or 2 mM lactose (C) then stimulated with anti-CD3ε antibody-coated beads for 10 min, and stained for TCR Enhanced TCR clustering was observed in 0/10, 1/10 and 9/10, respectively. (D) Mgat5$^{+/+}$ T cells incubated with increasing concentrations of disaccharide (1/3 serial dilution from 2.4 mM) and stimulated for 1 min with anti-CD3ε antibody-coated beads were compared for phosphotyrosine. Arrows at the right indicate the positions of molecular mass markers. A longer exposure of the lower molecular weight portion of the blot is shown. (E) Galectin-3 detected by surface labeling with NHS-biotin on T cells. Below, association of galectin-3 with CD3ε and TCRα chain, and its disruption by Mgat5 deficiency and lactose is shown. (F) A model depicting restricted mobility of TCR by interaction with a galectin—glycoprotein network, which is stronger in Mgat5-expressing cells. (G) LacZ activity in untreated (white) and anti-CD3 and anti-CD28 stimulated (grey) T cells from Mgat5$^{-/-}$ mice. (H) L-PHA binding to Mgat5$^{+/+}$ T lymphocytes either untreated (white) or stimulated with anti-CD3 and anti-CD28 for 48 h (grey).

The larger size of Mgat5-modified glycans may limit the geometry and spacing of TCR clusters in the plane of the membrane (24). Alternatively, Mgat5-modified glycans may bind cell surface galectins which restrict TCR mobility, thus antigen-induced TCR clustering. The galectins are a widely expressed family of mammalian lectins defined as N-acetyllactosamine-binding proteins. The poly N-acetyllactosamine sequences preferentially added to Mgat5-modified glycans (6), enhanced the affinity for galectin binding (FIG. 1A). Galectins bind lactosamine and lactose with dissociation constants in the 10$^{-4}$ M range (7; 8), an affinity comparable to MHC/peptide-induced oligomerization of TCRs in solution (22). Therefore, the avidity of a multivalent galectin—Mgat5 glycoprotein lattice at the cell surface may be sufficient to restrict TCR clustering. To probe for the presence of galectin—glycoprotein interactions, wild type ex vivo T cells were pre-incubated with various disaccharides for 20 min prior to a 10 min. stimulation with anti-CD3ε antibody coated beads. Pre-incubation with lactose increased TCR clustering at the bead interface and reduced TCR density elsewhere on the cells (FIG. 4C), which is similar to the behavior of untreated Mgat5$^{-/-}$ T cells (FIGS. 3A, B). TCR clustering was not altered by pre-incubation with the control disaccharide sucrose (FIG. 4B). Lactosamine and lactose both enhanced protein phosphorylation induced by anti-CD3ε antibody coated beads but sucrose and maltose had no effect (FIG. 4D and data not shown). Lactose did not enhance signaling in Mgat5$^{-/-}$ T cells (data not shown).

Galectin-3 was detected on the surface of naive T-cells by labeling with NHS-biotin, capture with streptavidin beads and Western blotting with anti-galectin-3 antibodies (FIG. 4E). Chemical crosslinking of the cell surface to stabilize complexes, followed by western blotting of galectin-3 immunoprecipitates demonstrated that galectin-3 is associated with TCR complex proteins. This interaction was disrupted by either Mgat5 deficiency or by incubating wild type T-cells with 2 mM lactose (FIG. 4E). Taken together, the data demonstrates that a multivalent cell surface galectin-glycoprotein lattice limits TCR clustering in response to agonist, the avidity of which is dependent upon Mgat5-modified glycans (FIG. 4F). The full complement of glycoproteins and lectins present in the T cell lattice remain to be defined but at a minimum includes galectin-3 and the TCR complex. Others have shown that exogenously added galectin-1 binds CD2, CD3, CD4, CD7, CD43 and CD45 and these proteins may also participate in the lattice (25). Indeed, exogenous galectin-1 modulates T cell activation in vitro (9; 25), antagonizes TCR signaling (26), and when injected into mice, it suppresses the pathology of EAE (27).

The gene replacement vector used to produce the Mgat5-deficient mice contained the reporter gene LacZ replacing the first exon, which was expressed with the same tissue-specificity as Mgat5 transcript (16). Both LacZ expression and cell-surface Mgat5-modified glycans in Mgat5$^{+/-}$ T cells, respectively, increased 48 h after stimulation demonstrating regulation of Mgat5 by transcriptional means (FIGS. 4G, H). This suggests that Mgat5 enzyme activity and glycan production are limiting in resting T cells, and with stimulation, increases in Mgat5-modified glycans and galectins may dampen TCR sensitivity to antigen. Negative feedback by Mgat5-modified glycans on TCR sensitivity is delayed as it requires Mgat5 gene expression, which is dependent on T cell activation status, and only indirectly on antigen concentrations. This form of slow-negative regulation governed by steady-state activity of the system is a key feature of robust and adaptive biochemical pathways (28) and Mgat5-modified glycans may contribute this feature to T cell regulation.

Viola et at have estimated that sustained clustering of ~8000 TCRs is required for T cell activation, but other molecular interactions clearly alter this threshold. With CD28 co-stimulation, only ~1500 TCRs are required (2). Co-signaling through CD28 decreases the extent of TCR clustering needed for activation predominantly by recruiting protein kinase-enriched GM1 ganglioside rafts to the site of TCR engagement, thereby amplifying signaling (3; 5). Here it is shown that Mgat5 deficiency increases the number of TCRs recruited to the antigen-presenting surface, thereby reducing the requirement for CD28 co-receptor engagement This may lead to T cell activation in the absence of CD28 co-signaling, failure of anergy and loss of immune tolerance. CD28$^{-/-}$ mice are resistant to induction of EAE by low dose MBP, while Mgat5$^{-/-}$ are hypersensitive, but both mutants develop clinical signs of EAE comparable to wild type littermates with high doses of MBP (29). In this regard, CD28 and Mgat5 appear to be opposing regulators of T cell activation thresholds, and susceptibility to autoimmune disease. In summary, Mgat5-dependent glycosylation limits agonist-induced TCR clustering by sequestering receptors in a cell surface galectin-glycoprotein lattice. However, the glycosylation deficiency in Mgat5$^{-/-}$ mice affects other pathways and cells types that may also contribute to the observed autoimmunity. Indeed, Mgat5-modified glycans also reduce clusters of fibronectin receptors causing accelerated focal adhesion turnover in fibroblasts and tumor cells; a functionality that may affect leukocyte motility (16). Finally, glycosylation of Notch receptor by Fringe, a fucose-specific β1,3GlcNAc-transferase provides another example of regulation by differential receptor glycosylation (30). In a broad context, the results described herein suggest a general mechanism for the regulation of receptor clustering through differential glycosylation and interaction with cell surface lectins.

TABLE 1

Clinical observations of autoimmune encephalomyelitis (EAE)

| Groups (dose) | Incidence of EAE | Peak score | Onset (days) | Days with disease | Deaths |
|---|---|---|---|---|---|
| Mgat5$^{+/+}$ (25 µg) | 3/11 | 0.45 ± 0.24 | 24 ± 3.9 | 7.0 ± 3.9 | 0 |
| Mgat5$^{-/-}$ (25 µg) | 9/11# | 1.82 ± 0.39* | 19.8 ± 3.3* | 11.5 ± 3.0* | 1 |
| Mgat5$^{+/+}$ (100 µg) | 10/10 | 1.6 ± 0.22 | 25 ± 2.2 | 18.5 ± 2.2 | 0 |
| Mgat5$^{-/-}$ (100 µg) | 10/10 | 2.1 ± 0.34* | 17.6 ± 2.9* | 23.3 ± 3.5* | 1 |
| Mgat5$^{+/+}$ (500 µg) | 12/12 | 3.0 ± 0.43 | 8.9 ± 1.2 | 27.9 ± 4.0 | 3 |
| Mgat5$^{-/-}$ (500 µg) | 12/12 | 2.83 ± 0.38 | 9.3 ± 0.95 | 27.2 ± 2.9 | 2 |

Disease severity was scored on a scale of 0-5; with 0, no illness; 1, limp tail, 2; limp tail and hindlimb weakness; 3, hindlimb paralysis; 4, forelimb weakness/paralysis and hindlimb paralysis; 5, moribund or death. Mean±SE of incidence, peak score, and days with disease were calculated using the total number of mice injected per dose as the denominator. The mean±SE for day-of-onset was determined by only using those mice that became sick. # Contingency test, P<0.001; and * Mann Whitney test comparing genotypes for significant differences at P<0.05.

REFERENCES

1. Valitutti, S., Mulle, S., Cella, M., Padovan, E., and Lanzavecchia, A. Serial triggering of many T-cell receptors by a few peptide-MHC complexes. *Nature* 375: 148-151 (1995).
2. Viola, A. and Lanzavecchia, A. T cell activation determined by T cell receptor number and tunable thresholds. *Science* 273: 104-106 (1996).
3. Viola, A., Schroeder, S., Sakakibara, Y., and Lanzavecchia, A. T lymphocyte costimulation mediated by reorganization of membrane microdomains. *Science* 283: 680-682 (1999).
4. Monks, C. R. Feiberg. B. A., Kupfer, H., Sciaky, N., and Kupfer, A. Three-dimensional segregation of supramolecular activation clusters in T cells. *Nature* 395: 82-86 (1998).
5. Wulfing, C. and Davis, M. M. A receptor/cytoskeletal movement triggered by costimulation during T cell activation. *Science*, 282: 2266-2269 (1998).
6. Cummings, R. D. and Kornfeld, S. The distribution of repeating Gal β1-4GlcNAc β1-3 sequences in asparagine-linked oligosaccharides of the mouse lymphoma cell line BW5147 and PHAR 2.1. *J. Biol. Chem.*, 259: 6253-6260 (1984).
7. Sato, S. and Hughes, R. C. Binding specificity of a baby hamster kidney lectin for H type I and II chains, polylactosamine glycans, and appropriately glycosylated forms of laminin and fibronectin. *J. Biol. Chem.*, 267: 6983-6990 (1992).
8. Knibbs R. N., Agrwal N., Wang J. L., and Goldstein I. J. Carbohydrate-binding protein 35. II. Analysis of the interaction of the recombinant polypeptide with saccharides. *J. Biol. Chem.*, 268: 14940-14947 (1993).
9. Perillo, N. L., Pace, K. E., Seilhamer, J. J., and Baum, L. G. Apoptosis of T cells mediated by galectin-1. *Nature*, 378: 736-739 (1995).
10. Vespa, G. N., Lewis, L. A., Kozak, K. R., Moran, M., Nguyen, J. T., Baum, L. G., and Miceli, M. C. Galectin-1 specifically modulates TCR signals to enhance TCR apoptosis but inhibit IL-2 production and proliferation. *J. Immunology*, 162: 799-806 (1999).
11. Karsan, A., Cornejo, C. J., Winn, R. K., Schwartz, B. R., Way, W., Lannir, N., Gershoni-Baruch, R., Etzioni, A., Ochs, H. D., and Harlan, J. M. Leukocyte Adhesion Deficiency Type II is a generalized defect of de novo GDP-fucose biosynthesis. Endothelial cell fucosylation is not required for neutrophil rolling on human nonlymphoid endothelium. *J. Clin. Invest.*, 101: 2438-2445 (1998).
12. Ellies, L. G., Tsuboi, S., Petryniak, B., Lowe, J. B., Fukuda, M., and Marth, J. D. Core 2 oligosaccharide biosynthesis distinguishes between selectin ligands essential for leukocyte homing and inflammation. *Immunity*, 9: 881-890 (1998).
13. Priatel, J. J., Chui, D., Hiraoka, N., Simmons, C. J., Richardson, K. B., Page, D. M., Fukuda, M., Varki, N. M., and Marth, J. D. The ST3Gal-I sialyltransferase controls CD8+T lymphocyte homeostasis by modulating O-glycan biosynthesis. *Immunity*, 12: 273-283 (2000).
14. Wall, K. A., Pierce, J. D., and Elbein, A. D. Inhibitors of glycoprotein processing alter T-cell proliferative responses to antigen and to interleukin 2. *Proc. Natl. Acad. Sci. USA*, 85: 5644-5648 (1988).
15. Cummings, R. D., Trowbridge, I. S., and Kornfeld, S. A mouse lymphoma cell line resistant to the leukoagglutinating lectin from Phaseolus vulgaris is deficient in UDP-GlcNAc:α-D-mannoside β1,6N-acetylglucosaminyltransferase. *J. Biol. Chem.*, 257: 13421-13427 (1982).
16. Granovsky, K, Fata, J., Pawling, J., Muller, W. J., Khokha, R. and Dennis, J. W. Suppression of tumor growth and metastasis in Mgat5-deficient mice. *Nature Medicine*, 6: 306-312 (2000).
17. Lafaille, J. J., Nagashima, K., Katsuki, M., and Tonegawa, S. High incidence of spontaneous autoimmune encephalomyelitis in immunodeficient anti-myelin basic protein T cell receptor transgenic mice. *Cell*, 78: 399-408 (1994).
18. Downward, J., Graves, J. D., Warne, P. H., Rayter, S., and Cantrell, D. A. Stimulation of p21$^{ras}$ upon Tell activation. *Nature*, 346: 719-723 (1990).
19. Trevillyan, J. M., Lu, Y. L., Atluru, D., Phillips, C. A., and Bjorndahl, J. M. Differential inhibition of T cell receptor signal transduction and early activation events by a selective inhibitor of protein-tyrosine kinase. *J. Immunology*, 145: 3223-3230 (1990).
20. Wang, J., Lim, K., Smolyar, A., Teng, M., Liu, J., Tse, A. G., Hussey, R. E., Chishti, Y., Thomson. C. T., Sweet, R. M., Nathenson, S. G., Chang, H. C., Sacchettini, J. C., and Reinherz, E. L. Atomic structure of an alphabeta T cell receptor (TCR) heterodimer in complex with an anti-TCR fab fragment derived from a mitogenic antibody. *EMBO J.*, 17: 10-26 (1998).
21. Hubbard, S. C., Kranz, D. M., Longmore, G. D., Sitkovsky, M. V., and Eisen, H. N. Glycosylation of the T-cell antigen-specific receptor and its potential role in lectin-mediated cytotoxicity. *Proc. Natl. Acad. Sci. USA,* 83: 1852-1856 (1986).
22. Reich Z, Boniface J J, Lyons D S, Borochov N, Wachtel E J, and Davis M M Ligand-specific oligomerization of T-cell receptor molecules. *Nature,* 387: 617-620 (1997).
23. Reif, K. and Cantrell, D. A. Networking Rho family GTPases in lymphocytes. *Immunity,* 8: 395-401, (1998).
24. Rudd, P. M., Wormald, M. R., Stanfield, R. L., Huang, M., Mattsson, N., Speir, J. A., DiGennaro, J. A., Fetrow, J. S., Dwek, R. A., and Wilson, I. A. Roles for glycosylation of cell surface receptors involved in cellular immune recognition. *J. Mol. Biol.,* 293: 351-366 (1999).
25. Pace, K. E., Lee, C., Stewart, P. L., and Baum, L. G. Restricted receptor segregation into membrane microdomains occurs on human T cells during apoptosis induced by galectin-1. *J. Immunology,* 163: 3801-3811 (1999).
26. Chung, C. D., Patel, V. P., Moran, M., Lewis, L. A., and Carrie Miceli, M. Galectin-1 induces partial TCR zeta-chain phosphorylation and antagonizes processive TCR signal transduction. *J. Immunology,* 165: 3722-3729 (2000).
27. Offner, H., Celnik, B., Bringman, T. S., Casentini-Borocz, D., Nedwin, G. E., and Vandenbark, A. A. Recombinant human beta-galactoside binding lectin suppresses clinical and histological signs of experimental autoimmune encephalomyelitis. *J. Neuroimmunol.,* 28: 177-184 (1990).
28. Barkal, N. and Leibler, S. Robustness in simple biochemical networks. *Nature,* 387: 913-917 (1997).
29. Oliveira-dos-Santos, A. J., Ho, A., Tada, Y., Lafaille J. J., Tonegawa, S., Mak T. W., and Penninger, J. M. CD28 costimulation is crucial for the development of spontaneous autoimmune encephalomyelitis. *J. Immunology,* 162: 4490-4495 (1999).
30. Moloney. D. J., Panin, V. M., Johnston, S. H., Chen, J., Shao, L., Wilson, R., Wang, Y., Stanley, P., Irvine, K. D., Haltiwanger, R. S., and Vogt, T. F. Fringe is a glycosyltransferase that modifies Notch. *Nature,* 406: 369-375 (2000).

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the cell lines, vectors, methodologies etc. which are reported therein which might be used in connection with the invention. Nothing herein is to be construed as an admission that the invention is not entitled to antedate such disclosure by virtue of prior invention.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

We claim:

1. A cell based assay for evaluating a test compound for its ability to regulate T cell receptor clustering comprising (a) providing T cells having galectin-3 associated with their T cell recptor and which are deficient in β1,6N-acetylglucosaminyltransferase V (Mgat5); (b) mixing the T cells, and a test compound under conditions which induce receptor clustering; (c) detecting receptor clustering; and (d) comparing to receptor clustering detected in T cells in the absence of a test compound wherein a difference in receptor clustering indicates that the test compound potentially regulates receptor clustering.

2. A cell based assay according to claim 1 wherein the cells are Mgat5$^{-/-}$ T cells.

3. A cell based assay according to claim 1 wherein T cell receptor clustering is induced by adding an antigen presenting cell or bead coated with an antigen or anti-TCR antibody.

4. A cell based assay according to claim 3 wherein T cell receptor clustering is induced by adding anti-CD3ϵ antibody coated beads.

* * * * *